(12) United States Patent
Mahapatra et al.

(10) Patent No.: US 11,951,303 B2
(45) Date of Patent: *Apr. 9, 2024

(54) STEERABLE EPICARDIAL PACING CATHETER SYSTEM PLACED VIA THE SUBXIPHOID PROCESS

(71) Applicant: UNIVERSITY OF VIRGINIA PATENT FOUNDATION, Charlottesville, VA (US)

(72) Inventors: Srijoy Mahapatra, Charlottesville, VA (US); George T. Gillies, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,137

(22) Filed: Apr. 23, 2018

(65) Prior Publication Data

US 2018/0361145 A1     Dec. 20, 2018

Related U.S. Application Data

(63) Continuation of application No. 12/741,710, filed as application No. PCT/US2008/082835 on Nov. 7, 2008, now abandoned.

(60) Provisional application No. 61/023,727, filed on Jan. 25, 2008, provisional application No. 60/986,786, filed on Nov. 9, 2007.

(51) Int. Cl.
*A61N 1/05* (2006.01)

(52) U.S. Cl.
CPC .................... *A61N 1/0587* (2013.01)

(58) Field of Classification Search
CPC ............................ A61N 1/0587; A61N 1/059
See application file for complete search history.

(56) References Cited

U.S. PATENT DOCUMENTS

| 579,288 A | 3/1897 | Beyl |
|---|---|---|
| 3,794,026 A | 2/1974 | Jacobs |
| 3,808,706 A | 5/1974 | Mosley et al. |

(Continued)

FOREIGN PATENT DOCUMENTS

| AU | 70522/96 | 1/1997 |
|---|---|---|
| BR | PI0809127-7 | 10/2019 |

(Continued)

OTHER PUBLICATIONS

Tomaske et al., "Do Daily Threshold Trend Fluctuations of Epicardial Leads Correlate with Pacing and Sensing Characteristics in Paediatric Patients," Eurospace, pp. 662-668 (2007).

(Continued)

*Primary Examiner* — Eric D. Bertram
(74) *Attorney, Agent, or Firm* — Jenkins, Taylor & Hunt, P.A.; Robert J. Decker

(57) ABSTRACT

The epicardial pacing system and related method includes an epicardial catheter configured to be disposed in the middle mediastinum of the thorax of a subject for use in electrical pacing of the heart at one or more locations on the epicardial surface. The epicardial pacing catheter may include at least one electrode whereby the electrode is insulated on at least one side to allow pacing of the heart without damage to adjacent anatomical structures.

5 Claims, 17 Drawing Sheets

(56) References Cited

U.S. PATENT DOCUMENTS

| | | |
|---|---|---|
| 3,814,104 A | 6/1974 | Irnich et al. |
| 4,142,530 A * | 3/1979 | Wittkampf ............ A61N 1/0587 607/116 |
| 4,167,070 A | 9/1979 | Orden |
| 4,263,918 A | 4/1981 | Swearingen et al. |
| 4,280,510 A | 7/1981 | O'Neill |
| 4,349,023 A | 9/1982 | Gross |
| 4,378,023 A * | 3/1983 | Trabucco ............ A61B 17/3468 607/120 |
| 4,607,644 A | 8/1986 | Pohndorf |
| 4,817,634 A | 4/1989 | Holleman |
| 4,935,008 A | 6/1990 | Lewis |
| 4,971,070 A | 11/1990 | Holleman |
| 4,991,603 A | 2/1991 | Cohen |
| 5,033,477 A | 7/1991 | Chin |
| 5,071,428 A | 12/1991 | Chin |
| 5,125,888 A | 6/1992 | Howard et al. |
| 5,158,097 A | 10/1992 | Christlieb |
| 5,176,153 A | 1/1993 | Eberhardt et al. |
| 5,213,570 A | 5/1993 | Van Deripe et al. |
| 5,269,326 A | 12/1993 | Verrier |
| 5,300,110 A | 4/1994 | Latterell |
| 5,335,313 A | 8/1994 | Douglas |
| 5,336,252 A | 8/1994 | Cohen |
| 5,395,349 A | 3/1995 | Quiachon |
| 5,465,711 A | 11/1995 | Moll |
| 5,484,423 A | 1/1996 | Waskonig |
| 5,500,012 A | 3/1996 | Brucker et al. |
| 5,509,924 A | 4/1996 | Paspa |
| 5,544,654 A | 8/1996 | Murphy |
| 5,662,647 A | 9/1997 | Crow et al. |
| 5,669,882 A | 9/1997 | Pyles |
| 5,679,005 A | 10/1997 | Einstein |
| 5,702,438 A | 12/1997 | Avitall |
| 5,707,335 A | 1/1998 | Howard et al. |
| 5,725,504 A | 3/1998 | Collins |
| 5,733,280 A | 3/1998 | Avitall |
| 5,779,694 A | 7/1998 | Howard et al. |
| 5,779,699 A | 7/1998 | Lipson |
| 5,792,217 A | 8/1998 | Camps et al. |
| 5,797,870 A | 8/1998 | March |
| 5,800,428 A | 9/1998 | Nelson |
| 5,807,249 A | 9/1998 | Qin et al. |
| 5,812,978 A | 9/1998 | Nolan |
| 5,814,012 A | 9/1998 | Fleenor et al. |
| 5,827,216 A | 10/1998 | Igo |
| 5,843,048 A | 12/1998 | Gross |
| 5,846,239 A | 12/1998 | Swanson |
| 5,868,741 A | 2/1999 | Chia et al. |
| 5,885,217 A | 3/1999 | Gisselberg |
| 5,899,937 A | 5/1999 | Goldstein et al. |
| 5,916,194 A | 6/1999 | Jacobsen et al. |
| 5,928,191 A | 7/1999 | Houser et al. |
| 5,931,810 A | 8/1999 | Grabek |
| 5,970,457 A | 10/1999 | Brant |
| 5,972,013 A | 10/1999 | Schmidt |
| 6,032,674 A | 3/2000 | Eggers et al. |
| 6,036,685 A | 3/2000 | Mueller et al. |
| 6,051,008 A | 4/2000 | Saadat |
| 6,062,866 A | 5/2000 | Prom |
| 6,120,476 A | 9/2000 | Fung et al. |
| 6,123,084 A | 9/2000 | Jandak et al. |
| 6,148,825 A | 11/2000 | Anderson |
| 6,156,009 A | 12/2000 | Grabek |
| 6,156,018 A | 12/2000 | Hassett |
| 6,162,195 A | 12/2000 | Igo |
| 6,200,303 B1 | 3/2001 | Verrier |
| 6,200,315 B1 | 3/2001 | Gaiser et al. |
| 6,206,004 B1 | 3/2001 | Schmidt |
| 6,206,874 B1 | 3/2001 | Ubby et al. |
| 6,216,030 B1 | 4/2001 | Howard et al. |
| 6,216,704 B1 | 4/2001 | Ingle et al. |
| 6,231,518 B1 | 5/2001 | Grabek |
| 6,234,804 B1 | 5/2001 | Yong |
| 6,237,605 B1 | 5/2001 | Vaska et al. |
| 6,245,440 B1 | 6/2001 | Kuhlmann-Wilsdorf et al. |
| 6,263,241 B1 | 7/2001 | Rosborough et al. |
| 6,266,567 B1 | 7/2001 | Ishikawa |
| 6,270,476 B1 | 8/2001 | Santoianni et al. |
| 6,270,484 B1 | 8/2001 | Yoon |
| 6,272,370 B1 | 8/2001 | Gillies et al. |
| 6,273,877 B1 | 8/2001 | West |
| 6,278,975 B1 | 8/2001 | Brant |
| 6,298,259 B1 | 10/2001 | Kucharczyk et al. |
| 6,314,963 B1 | 11/2001 | Vaska et al. |
| 6,322,536 B1 | 11/2001 | Rosengart |
| 6,325,776 B1 | 12/2001 | Anderson |
| 6,416,505 B1 | 7/2002 | Fleischman |
| 6,423,051 B1 | 7/2002 | Kaplan |
| 6,443,735 B1 | 9/2002 | Eggert |
| 6,500,130 B2 | 12/2002 | Kinsella et al. |
| 6,527,767 B2 | 3/2003 | Wang et al. |
| 6,551,289 B1 | 4/2003 | Higuchi |
| 6,554,809 B2 | 4/2003 | Aves |
| 6,558,382 B2 | 5/2003 | Jahns |
| 6,569,082 B1 | 5/2003 | Chin |
| 6,592,552 B1 | 7/2003 | Schmidt |
| 6,599,274 B1 | 7/2003 | Kucharcyzk et al. |
| 6,602,242 B1 | 8/2003 | Fung et al. |
| 6,613,062 B1 | 9/2003 | Leckrone |
| 6,616,676 B2 | 9/2003 | Bashiri et al. |
| 6,626,902 B1 | 9/2003 | Kucharczyk et al. |
| 6,666,844 B1 | 12/2003 | Igo |
| 6,666,861 B1 | 12/2003 | Grabek |
| 6,689,128 B2 | 2/2004 | Sliwa |
| 6,711,436 B1 | 3/2004 | Duhaylongsod |
| 6,723,092 B2 | 4/2004 | Brown |
| 6,752,805 B2 | 6/2004 | Maguire |
| 6,771,996 B2 | 8/2004 | Bowe |
| 6,783,510 B1 | 8/2004 | Gibson et al. |
| 6,786,898 B2 | 9/2004 | Guenst |
| 6,811,544 B2 | 11/2004 | Schaer |
| 6,827,714 B2 | 12/2004 | Swanson |
| 6,827,715 B2 | 12/2004 | Francischelli |
| 6,834,201 B2 | 12/2004 | Gillies et al. |
| 6,835,193 B2 | 12/2004 | Epstein et al. |
| 6,837,848 B2 | 1/2005 | Bonner |
| 6,837,886 B2 | 1/2005 | Collins et al. |
| 6,849,075 B2 | 2/2005 | Bertolero |
| 6,868,291 B1 | 3/2005 | Bonner et al. |
| 6,869,414 B2 | 3/2005 | Simpson et al. |
| 6,874,501 B1 | 4/2005 | Estetter et al. |
| 6,876,885 B2 | 4/2005 | Swoyer et al. |
| 6,899,710 B2 | 5/2005 | Hooven |
| 6,916,318 B2 | 7/2005 | Francischelli |
| 6,918,890 B2 | 7/2005 | Schmidt |
| 6,918,908 B2 | 7/2005 | Bonner et al. |
| 6,921,295 B2 | 7/2005 | Sommer et al. |
| 6,928,313 B2 | 8/2005 | Peterson |
| 6,936,040 B2 | 8/2005 | Kramm et al. |
| 6,960,205 B2 | 11/2005 | Jahns |
| 6,968,223 B2 | 11/2005 | Hanover |
| 6,973,352 B1 | 12/2005 | Tsutsui et al. |
| 6,974,454 B2 | 12/2005 | Hooven |
| 7,004,937 B2 | 2/2006 | Lentz et al. |
| 7,008,418 B2 | 3/2006 | Hall et al. |
| 7,027,876 B2 | 4/2006 | Casavant et al. |
| 7,037,296 B2 | 5/2006 | Kadziauskas |
| 7,041,099 B2 | 5/2006 | Thomas et al. |
| 7,048,733 B2 | 5/2006 | Hartley et al. |
| 7,059,878 B1 | 6/2006 | Hendrixson |
| 7,063,693 B2 | 6/2006 | Guenst |
| 7,085,606 B2 | 8/2006 | Flach |
| 7,089,063 B2 | 8/2006 | Lesh et al. |
| 7,090,637 B2 | 8/2006 | Danitz et al. |
| 7,101,362 B2 | 9/2006 | Vanney |
| 7,104,986 B2 | 9/2006 | Hovda |
| 7,120,504 B2 | 10/2006 | Osypka |
| 7,130,699 B2 | 10/2006 | Huff et al. |
| 7,142,919 B2 | 11/2006 | Hine et al. |
| 7,146,225 B2 | 12/2006 | Guenst |
| 7,147,633 B2 | 12/2006 | Chee |
| 7,207,988 B2 | 4/2007 | Leckrone |
| 7,214,180 B2 | 5/2007 | Chin |

(56) References Cited

U.S. PATENT DOCUMENTS

| | | |
|---|---|---|
| 7,226,448 B2 | 6/2007 | Bertolero |
| 7,226,458 B2 | 6/2007 | Kaplan et al. |
| 7,232,422 B2 | 6/2007 | Gibson et al. |
| 7,247,139 B2 | 7/2007 | Yudkovitch |
| 7,259,906 B1 | 8/2007 | Islam |
| 7,264,587 B2 | 9/2007 | Chin |
| 7,286,992 B2 | 10/2007 | Sander |
| 7,309,328 B2 | 12/2007 | Kaplan |
| 7,398,781 B1 | 7/2008 | Chin |
| 7,468,029 B1 | 12/2008 | Robertson |
| 7,473,244 B2 | 1/2009 | Frazier |
| 7,670,327 B2 | 3/2010 | Kucharczyk et al. |
| 7,727,225 B2 | 6/2010 | Broaddus et al. |
| 8,048,072 B2 | 11/2011 | Verin et al. |
| 8,096,984 B2 | 1/2012 | Kucharczyk et al. |
| 8,211,083 B2 | 7/2012 | Broaddus et al. |
| 8,226,694 B2 | 7/2012 | Broaddus et al. |
| 8,255,193 B2 | 8/2012 | Humphrey et al. |
| 8,271,095 B2 | 9/2012 | O'Sullivan |
| 8,282,565 B2 | 10/2012 | Mahapatra et al. |
| 8,655,798 B2 | 2/2014 | Humphrey et al. |
| 8,728,053 B2 | 5/2014 | Broaddus et al. |
| 8,906,056 B2 | 12/2014 | Gillies et al. |
| 9,211,405 B2 * | 12/2015 | Mahapatra .......... A61B 18/1492 |
| 9,218,752 B2 | 12/2015 | Gillies et al. |
| 9,314,265 B2 | 4/2016 | Mahapatra et al. |
| 9,364,660 B2 | 6/2016 | Howard et al. |
| 9,468,396 B2 | 10/2016 | Mahapatra et al. |
| 9,636,487 B2 | 5/2017 | Utz et al. |
| 9,642,534 B2 | 5/2017 | Mahapatra et al. |
| 10,166,066 B2 | 1/2019 | Mahapatra et al. |
| 10,702,335 B2 | 7/2020 | Mahapatra et al. |
| 11,058,354 B2 | 7/2021 | Mahapatra et al. |
| 11,083,381 B2 | 8/2021 | Mahapatra et al. |
| 2001/0001314 A1 | 5/2001 | Davison et al. |
| 2001/0020166 A1 | 9/2001 | Daly |
| 2001/0024735 A1 | 9/2001 | Kuhlmann-Wilsdorf et al. |
| 2001/0025178 A1 | 9/2001 | Mulier et al. |
| 2001/0039410 A1 | 11/2001 | Verrier |
| 2001/0056280 A1 | 12/2001 | Underwood et al. |
| 2002/0002372 A1 | 1/2002 | Jahns et al. |
| 2002/0019626 A1 | 2/2002 | Sharkey et al. |
| 2002/0045895 A1 | 4/2002 | Sliwa |
| 2002/0055714 A1 | 5/2002 | Rothschild |
| 2002/0058925 A1 | 5/2002 | Kaplan |
| 2002/0072737 A1 | 6/2002 | Belden et al. |
| 2002/0077600 A1 | 6/2002 | Sirimanne |
| 2002/0082523 A1 | 6/2002 | Kinsella et al. |
| 2002/0103430 A1 | 8/2002 | Hastings et al. |
| 2002/0161361 A1 | 10/2002 | Sherman |
| 2003/0028187 A1 | 2/2003 | Vaska et al. |
| 2003/0050681 A1 * | 3/2003 | Pianca .................. A61N 1/057 607/125 |
| 2003/0065318 A1 | 4/2003 | Pendekanti |
| 2003/0069572 A1 | 4/2003 | Wellman et al. |
| 2003/0114796 A1 | 6/2003 | Schmidt |
| 2003/0181855 A1 | 9/2003 | Simpson et al. |
| 2003/0204171 A1 | 10/2003 | Kucharczyk et al. |
| 2004/0024397 A1 | 2/2004 | Griffin |
| 2004/0024413 A1 | 2/2004 | Lentz et al. |
| 2004/0024435 A1 | 2/2004 | Leckrone |
| 2004/0033477 A1 | 2/2004 | Ramphal et al. |
| 2004/0034365 A1 | 2/2004 | Lentz et al. |
| 2004/0064138 A1 | 4/2004 | Grabek |
| 2004/0068312 A1 | 4/2004 | Sigg et al. |
| 2004/0087831 A1 | 5/2004 | Michels et al. |
| 2004/0087938 A1 | 5/2004 | Leckrone |
| 2004/0102804 A1 | 5/2004 | Chin |
| 2004/0126746 A1 | 7/2004 | Toly |
| 2004/0138526 A1 | 7/2004 | Guenst |
| 2004/0138527 A1 | 7/2004 | Bonner |
| 2004/0138531 A1 | 7/2004 | Bonner |
| 2004/0147826 A1 | 7/2004 | Peterson |
| 2004/0176679 A1 | 9/2004 | Murphy et al. |
| 2004/0186507 A1 | 9/2004 | Hall et al. |
| 2004/0215168 A1 | 10/2004 | Verrier |
| 2004/0216748 A1 | 11/2004 | Chin |
| 2004/0267303 A1 | 12/2004 | Guenst |
| 2004/0267326 A1 | 12/2004 | Ocel et al. |
| 2005/0004514 A1 | 1/2005 | Hochman |
| 2005/0010205 A1 | 1/2005 | Hovda |
| 2005/0020914 A1 | 1/2005 | Amundson et al. |
| 2005/0027243 A1 | 2/2005 | Gibson |
| 2005/0085769 A1 | 4/2005 | MacMahon |
| 2005/0096522 A1 | 5/2005 | Reddy et al. |
| 2005/0107678 A1 | 5/2005 | Bowe |
| 2005/0119556 A1 | 6/2005 | Gillies et al. |
| 2005/0149152 A1 * | 7/2005 | Bertolero .......... A61B 18/1442 607/96 |
| 2005/0154376 A1 | 7/2005 | Riviere |
| 2005/0215945 A1 | 9/2005 | Harris et al. |
| 2005/0234507 A1 | 10/2005 | Geske |
| 2005/0251094 A1 | 11/2005 | Peterson |
| 2005/0256368 A1 | 11/2005 | Klenk |
| 2005/0261673 A1 | 11/2005 | Bonner |
| 2005/0273006 A1 | 12/2005 | Stewart |
| 2005/0273144 A1 | 12/2005 | Lennox |
| 2006/0025705 A1 | 2/2006 | Whittaker et al. |
| 2006/0025762 A1 | 2/2006 | Mohan et al. |
| 2006/0036307 A1 * | 2/2006 | Zarembo ................ A61N 1/056 607/122 |
| 2006/0041243 A1 | 2/2006 | Nayak |
| 2006/0052660 A1 | 3/2006 | Chin |
| 2006/0064056 A1 | 3/2006 | Coyle et al. |
| 2006/0064058 A1 | 3/2006 | Coyle |
| 2006/0074397 A1 | 4/2006 | Shimada |
| 2006/1016442 | 5/2006 | Richardson |
| 2006/0122591 A1 | 6/2006 | Keidar et al. |
| 2006/0189840 A1 | 8/2006 | Walsh |
| 2006/0200002 A1 | 9/2006 | Guenst |
| 2006/0229490 A1 | 10/2006 | Chin |
| 2006/0247522 A1 | 11/2006 | McGee |
| 2006/0247672 A1 | 11/2006 | Vidlund |
| 2006/0259017 A1 | 11/2006 | Heil |
| 2006/0270900 A1 | 11/2006 | Chin et al. |
| 2006/0271032 A1 | 11/2006 | Chin |
| 2007/0016068 A1 | 1/2007 | Grunwald et al. |
| 2007/0016069 A1 | 1/2007 | Grunwald |
| 2007/0016070 A1 | 1/2007 | Grunwald et al. |
| 2007/0016072 A1 | 1/2007 | Grunwald et al. |
| 2007/0032796 A1 | 2/2007 | Chin-Chen |
| 2007/0038052 A1 | 2/2007 | Swoyer et al. |
| 2007/0043397 A1 | 2/2007 | Ocel |
| 2007/0055142 A1 | 3/2007 | Webler |
| 2007/0198041 A1 | 8/2007 | Rupp |
| 2007/0270882 A1 | 11/2007 | Hjelle |
| 2007/0270928 A1 * | 11/2007 | Erlebacher .......... A61N 1/0563 607/126 |
| 2008/0015625 A1 | 1/2008 | Ventura et al. |
| 2008/0051671 A1 | 2/2008 | Broome |
| 2008/0051864 A1 * | 2/2008 | Callas .................. A61N 1/059 607/130 |
| 2008/0091109 A1 | 4/2008 | Abraham |
| 2008/0097399 A1 | 4/2008 | Sachar |
| 2008/0108945 A1 | 5/2008 | Kaplan |
| 2008/0183080 A1 | 7/2008 | Abraham |
| 2008/0208184 A1 | 8/2008 | Davies |
| 2008/0262432 A1 | 10/2008 | Miller |
| 2008/0262467 A1 | 10/2008 | Humphrey et al. |
| 2008/0294174 A1 | 11/2008 | Bardsley |
| 2008/0300618 A1 * | 12/2008 | Gertner ............ A61B 17/1114 606/192 |
| 2009/0030469 A1 | 1/2009 | Meiry |
| 2009/0048577 A1 | 2/2009 | Gillies et al. |
| 2009/0068627 A1 | 3/2009 | Toly |
| 2009/0069697 A1 | 3/2009 | Frazier |
| 2009/0192487 A1 | 7/2009 | Broaddus et al. |
| 2009/0246747 A1 | 10/2009 | Buckman |
| 2009/0253102 A1 | 10/2009 | Porikli et al. |
| 2009/0311656 A1 | 12/2009 | Lundback et al. |
| 2010/0042158 A1 | 2/2010 | Broaddus et al. |
| 2010/0069849 A1 | 3/2010 | Kassab |
| 2010/0094143 A1 | 4/2010 | Mahapatra |
| 2010/0114093 A1 | 5/2010 | Mahapatra |

(56) References Cited

U.S. PATENT DOCUMENTS

| | | |
|---|---|---|
| 2010/0167251 A1 | 7/2010 | Boutchko et al. |
| 2010/0210927 A1 | 8/2010 | Gillies et al. |
| 2010/0211064 A1 | 8/2010 | Mahapatra |
| 2010/0241185 A1 | 9/2010 | Mahapatra |
| 2012/0249890 A1 | 10/2012 | Chardon et al. |
| 2012/0274863 A1 | 11/2012 | Chardon et al. |
| 2012/0278348 A1 | 11/2012 | Chardon et al. |
| 2012/0283582 A1 | 11/2012 | Mahapatra et al. |
| 2012/0310052 A1 | 12/2012 | Mahapatra |
| 2012/0330184 A1 | 12/2012 | Mahapatra |
| 2013/0085386 A1 | 4/2013 | Humphrey et al. |
| 2013/0090556 A1 | 4/2013 | Broaddus et al. |
| 2013/0096428 A1 | 4/2013 | Gillies et al. |
| 2013/0108999 A1 | 5/2013 | Gillies |
| 2013/0225904 A1 | 8/2013 | Gillies et al. |
| 2013/0303967 A1 | 11/2013 | Utz et al. |
| 2014/0128955 A1 | 5/2014 | Howard et al. |
| 2015/0297073 A1 | 10/2015 | Nguyen et al. |
| 2016/0100797 A1 | 4/2016 | Mahapatra et al. |
| 2016/0331445 A1 | 11/2016 | Mahapatra et al. |
| 2017/0086707 A1 | 3/2017 | Mahapatra et al. |
| 2017/0238823 A1 | 8/2017 | Mahapatra et al. |
| 2019/0274757 A1 | 9/2019 | Mahapatra et al. |

FOREIGN PATENT DOCUMENTS

| | | |
|---|---|---|
| CA | 2236958 | 5/1998 |
| CA | 2236958 | 11/1998 |
| DE | 4313903 C1 | 9/1994 |
| EP | 0134367 A1 | 3/1985 |
| EP | 0417171 B1 | 3/1991 |
| EP | 0450608 A1 | 10/1991 |
| EP | 1129681 A1 | 9/2001 |
| EP | 1181896 A1 | 2/2002 |
| EP | 2279773 | 2/2011 |
| EP | 2134253 | 1/2022 |
| WO | WO 87/04081 | 7/1987 |
| WO | WO 93/20878 | 10/1993 |
| WO | WO 93/20886 | 10/1993 |
| WO | WO 95/10319 | 4/1995 |
| WO | WO 95/15115 | 6/1995 |
| WO | WO 97/33526 | 9/1997 |
| WO | WO1997/037847 | 10/1997 |
| WO | WO1998/00060 | 1/1998 |
| WO | WO 99/18869 | 4/1999 |
| WO | WO00/007652 | 2/2000 |
| WO | WO00/23000 | 4/2000 |
| WO | WO 01/05306 | 1/2001 |
| WO | WO 01/58373 | 8/2001 |
| WO | WO 01/68173 | 9/2001 |
| WO | WO 01/80724 | 11/2001 |
| WO | WO 01/80757 | 11/2001 |
| WO | WO 01/93930 | 12/2001 |
| WO | WO2002/074358 | 9/2002 |
| WO | WO 03/092792 A2 | 11/2003 |
| WO | WO06/15091 | 2/2006 |
| WO | WO06/089243 | 8/2006 |
| WO | WO 2006113267 | 10/2006 |
| WO | WO 2007/081842 | 7/2007 |
| WO | WO 2008/02595 | 1/2008 |
| WO | WO 2008/013709 | 1/2008 |
| WO | WO 2008/057370 | 5/2008 |
| WO | WO 2008/112870 | 9/2008 |
| WO | WO 2008/115745 | 9/2008 |
| WO | WO 2008/118737 | 10/2008 |
| WO | WO 2009/062061 | 5/2009 |
| WO | WO 2010127259 A1 | 11/2010 |
| WO | WO 2011/103456 | 8/2011 |
| WO | WO 2011102874 A1 | 8/2011 |
| WO | WO2011/160080 | 12/2011 |
| WO | WO/2012/065125 | 5/2012 |

OTHER PUBLICATIONS

D'Avila et al., "Transthoracic Epicardial Catheter Ablation of Ventricular Tachycardia," Heart Rhythymn, vol. 3, pp. 1110-1111, (2006).

Sosa et al., "Epicardial Mapping and Ablation Techniques to Control Ventricular Tachycardia,"Journal of Cardiovascular Electrophysiology, vol. 16, pp. 449-452 (2005).

Mahapatra et al., "Incidence and Predictors of Cardiac Perforation after permanent Pacemaker Placement," Heart Rhythmn, vol. 2, pp. 907-911, (2005).

Packer et al., "Multimodality 3-D Ultrasound and Computed Tomographic Image Fusion: A Novel Basis for Catheter Navigation and Electroanatomic Mapping," Circulation, vol. 112, p. U684, (2005).

Sosa et al., "Nonsurgical Transthoracic Epicardial Approach in Patients with Ventricular Tachycardia and Previous Cardiac Surgery," Journal of Interventional Cardiac Electrophysiology, vol. 10, pp. 281-288, (2004).

Sosa, "Percutaneous Pericardia! Access for Mapping and Ablation of Epicardial Ventricular Tachycardias," Circulation, Journal of the American Heart Association, p. e542-e544, vol. 115 (2007).

Derose et al., "Robotically Assisted Left Ventricular Epicardial Lead Implantation for Biventricular Pacing: the Posterior Approach," Annals of Thoracic Surgery, vol. 77, pp. 1472-1474, (2004).

Hansky et al., "Lead Selection and Implantation Technique for Biventricular Pacing," European Heart Journal Supplements, vol. 6, pp. D112-D116, (2004).

Mair et al., "Epicardial Lead Implantation Techniques for Biventricular Pacing via Left Lateral Mini-Thoracotomy, Video-Assisted Thoracoscopy, and Robotic Approach," The Heart Surgery Forum, vol. 6, pp. 2003-4883 (2003).

Sarabanda et al., "Efficacy and Safety of Circumferential Pulmonary Vein Isolation Using a Novel Cryothermal Balloon Ablation System," Journal of the American College of Cardiology, vol. 46, pp. 1902-1912 (2005).

Mahapatra et al., "Access Device and Manometric Monitoring System for Epicardial Electrophysiology: Improved Porototype and Use in Human Trials," Jan. 2008 Technical Report UVA/640419/MAE08/102 (2008).

Mahapatra et al., "Access Device and Manometric Monitoring System for Epicardial Electrophysiology: Improved Porototype and Use in Human Trials," Jul. 2007 Technical Report UVA/640419/MAE08/101 (2007).

Thomas, "Analysis of Human Epidural Pressures," Regional Anesthesia, vol. 17, No. 4 pp. 212-215 (1992).

Moses, "Sirolimus-Eluting Stents Versus Standard Stents in Patients with Stenosis in a Native Coronary Artery", New England Journal of Medicine, vol. 349, No. 14 pp. 1315-1323 (2003).

Lin, "Catheter Microwave Ablation Therapy for Cardiac Arrhythmias," Bioelectromagnetics, vol. 20, pp. 120-132 (1999).

Klein, "Radiofrequency Ablation of Cardiac Arrhythmias," Scientific American Science & Medicine, p. 48-57 (1994).

Frolich, "Pioneers in Epidural Needle Design," Anesthesia & Analgesia, vol. 93 pp. 215-220 (2001).

Beukema, "Radiofrequency Ablation of Atrial Fibrillation in Patients Undergoing Concommitant CardiacSurgery: First Experience," PACE, vol. 20, p. 1100 (1997).

Arrow International Corporation, AN-05505 Epidural Needle, www.arrowintl.com/products/boms/AN05505.asp?

PX26 Series Pressure Transducers: Instruction Sheet, OMEGA Engineering, Inc., 2004 (accessed Dec. 5, 2007), Stamford, CT. Online at http://www.omega.com/Manuals/manualpdf/M1608.pdf.

PX26 Series Pressure Transducers: Instruction Sheet, OMEGA Engineering, Inc., 2004 (accessed Jul. 9, 2007), Stamford, CT. Online at http//www.omega.com/Pressure/pdf/PX26.pdf.

DPI 603 Portable Pressure Calibrator User Guide, OMEGA Engineering, Inc., 1996 (accessed Dec. 5, 2007), Stamford, CT. Online at http://www.omega.com/Manuals/manual.pdf/M2913.pdf.

DP41B Universal Input Meter: User's Guide, OMEGA Engineering, Inc., 2005 (accessed Dec. 5, 2007), Stamford, CT. Online at http://www.omega.com/Manuals/manualpdf.M2544.pdf.

DP25B-S Strain Gage Pagel Meter: User's Guide, OMEGA Engineering, Inc., 2002 (accessed Jul. 9, 2007), Stamford, CT. Online at http://www.omega.com/Manuals/manualpdf/M3598.pdf.

(56) References Cited

OTHER PUBLICATIONS

Stokes, U.S. Statutory Invention Registration H356, Nov. 3, 1987.
Advisory Action corresponding to U.S. Appl. No. 13/464,752 dated Dec. 31, 2015.
Advisory Action Notice of Allowance corresponding to U.S. Appl. No. 12/530,938 dated May 12, 2016.
Aliot et al., "EHRA/HRS expert consensus on catheter albation of ventricular arrhythmias," Europace, vol. 11, No. 6, pp. 771-817, 2009.
Aupperle et al., "Ablation of Atrial Fibrillation and Esophageal Injury: Effects of Energy Source and Ablation Technique," Journal of Thoracic and Cardiovascular Surgery, vol. 130, No. 6, pp. 1549-1554, (2005).
Intent to Grant corresponding to European Patent Application No. 08743794.3 dated Feb. 18, 2021.
International Preliminary Report on Patentability, Written Opinion, and International Search Report corresponding to International Patent Application No. PCT/US2008/057626 dated Sep. 22, 2009.
International Search Report corresponding to International Application No. PCT/US2011025470 dated Nov. 3, 2011.
Muller et al., "Application of CVD-diamond for catheter ablation in the heart," Diamond and Related Materials, vol. 13, pp. 1080-1083 (2004).
Notice of Allowance corresponding to corresponding to Brazilian Patent Application No. PI0809127-7 dated May 27, 2019.
Notice of Allowance corresponding to U.S. Appl. No. 12/532,233 dated Apr. 2, 2015.
Notice of Allowance corresponding to U.S. Appl. No. 12/530,830 dated Jun. 11, 2012.
Notice of Allowance corresponding to U.S. Appl. No. 12/530,860 dated Apr. 22, 2013.
Notice of Allowance corresponding to U.S. Appl. No. 12/530,938 dated Oct. 30, 2018.
Notice of Allowance corresponding to U.S. Appl. No. 13/464,752 dated Jan. 6, 2017.
Notice of Allowance corresponding to U.S. Appl. No. 13/464,762 dated Aug. 3, 2016.
Notice of Allowance corresponding to U.S. Appl. No. 13/607,993 dated Dec. 8, 2015.
Notice of Allowance corresponding to U.S. Appl. No. 14,879,849 dated Sep. 16, 2019.
Notice of Allowance corresponding to U.S. Appl. No. 14,879,849 dated Mar. 10, 2021.
Notice of Allowance corresponding to U.S. Appl. No. 14/967,923 dated Feb. 24, 2020.
Notice of Allowance corresponding to U.S. Appl. No. 15/295,102 dated Jan. 25, 2021.
Notice of Allowance corresponding to U.S. Appl. No. 15/295,102 dated Jul. 21, 2021.
Notice of Allowance corresponding to U.S. Appl. No. 15/589,522 dated Dec. 16, 2020.
Notice of Allowance corresponding to U.S. Appl. No. 15/589,522 dated Mar. 24, 2021.
Notification of Transmittal of International Preliminary Report on Patentability corresponding to PCT/US2008/056643 dated Aug. 19, 2009.
Office Action corresponding to Brazilian Patent Application No. PI0809127-7 dated Nov. 27, 2018.
Office Action (Advisory Action) corresponding to U.S. Appl. No. 13/464,762 dated Dec. 17, 2015.
Office Action (Restriction Requirement) corresponding to corresponding to U.S. Appl. No. 13/464,762 dated May 23, 2013.
Office Action (Restriction Requirement) corresponding to U.S. Appl. No. 12/530,938 dated Mar. 21, 2012.
Office Action (Restriction Requirement) corresponding to U.S. Appl. No. 12/741,710 dated Aug. 22, 2012.
Office Action (Restriction Requirement) corresponding to U.S. Appl. No. 14,879,849 dated Apr. 25, 2018.
Office Action (Restriction Requirement) corresponding to U.S. Appl. No. 13/464,762 dated May 23, 2013.
Office Action corresponding to European Patent Application No. 10846297.9 dated Jul. 1, 2014.
Office Action corresponding to U.S. Appl. No. 13/464,752 dated Dec. 4, 2014.
Office Action corresponding to U.S. Appl. No. 14/967,923 dated May 14, 2018.
Office Action corresponding to U.S. Appl. No. 14/967,923 dated Nov. 19, 2018.
Office Action corresponding to U.S. Appl. No. 12/530,860 dated Oct. 5, 2012.
Office Action corresponding to U.S. Appl. No. 12/530,938 dated Jun. 25, 2012.
Office Action corresponding to U.S. Appl. No. 12/530,938 dated Feb. 26, 2013.
Office Action corresponding to U.S. Appl. No. 12/530,938 dated Nov. 21, 2013.
Office Action corresponding to U.S. Appl. No. 12/530,938 dated Dec. 4, 2014.
Office Action corresponding to U.S. Appl. No. 12/530,938 dated Sep. 30, 2015.
Office Action corresponding to U.S. Appl. No. 12/532,233 dated Mar. 7, 2012.
Office Action corresponding to U.S. Appl. No. 12/532,233 dated Oct. 26, 2012.
Office Action corresponding to U.S. Appl. No. 12/532,233 dated May 15, 2013.
Office Action corresponding to U.S. Appl. No. 12/532,233 dated Aug. 7, 2014.
Office Action corresponding to U.S. Appl. No. 12/532,233 dated Aug. 14, 2015.
Office Action corresponding to U.S. Appl. No. 12/741,710 dated Jul. 3, 2013.
Office Action corresponding to U.S. Appl. No. 12/741,710 dated Apr. 22, 2014.
Office Action corresponding to U.S. Appl. No. 12/741,710 dated Jun. 15, 2015.
Office Action corresponding to U.S. Appl. No. 12/741,710 dated Nov. 8, 2012.
Office Action corresponding to U.S. Appl. No. 13/464,752 dated Mar. 7, 2014.
Office Action corresponding to U.S. Appl. No. 13/464,752 dated Jul. 10, 2015.
Office Action corresponding to U.S. Appl. No. 13/464,752 dated Aug. 2, 2016.
Office Action corresponding to U.S. Appl. No. 13/607,993 dated Jan. 12, 2015.
Office Action corresponding to U.S. Appl. No. 13/607,993 dated Aug. 14, 2014.
Office Action corresponding to U.S. Appl. No. 15/295,102 dated Jun. 13, 2019.
Office Action corresponding to U.S. Appl. No. 15/589,522 dated Jul. 8, 2019.
Office Action corresponding to U.S. Appl. No. 15/589,522 dated Feb. 21, 2020.
Office Action corresponding to U.S. Appl. No. 14/879,849 dated Sep. 10, 2018.
Office Action corresponding to U.S. Appl. No. 14/879,849 dated May 1, 2019.
Office Action corresponding to U.S. Appl. No. 14/879,849 dated Aug. 5, 2020.
Office Action corresponding to U.S. Appl. No. 13/464,762 dated Jul. 16, 2013.
Office Action corresponding to U.S. Appl. No. 13/464,762 dated Mar. 6, 2014.
Office Action corresponding to U.S. Appl. No. 13/464,762 dated Nov. 12, 2014.
Office Action corresponding to U.S. Appl. No. 13/464,762 dated Aug. 25, 2015.
Office Action corresponding to U.S. Appl. No. 13/464,762 dated Mar. 2, 2016.
Office Action corresponding to U.S. Appl. No. 13/579,882 dated Jan. 13, 2015.

(56) References Cited

OTHER PUBLICATIONS

Office Action corresponding to U.S. Appl. No. 15/295,102 dated Sep. 28, 2018.
Office Action corresponding to U.S. Appl. No. 15/295,102 dated Jul. 9, 2020.
Office Action corresponding to U.S. Appl. No. 16/236,664 dated Dec. 17, 2020.
Office Action corresponding to U.S. Appl. No. 16/236,664 dated May 24, 2021.
Patent Board Decision corresponding to U.S. Appl. No. 12/530,938 dated Sep. 25, 2018.
Patent Board Decision corresponding to U.S. Appl. No. 12/741,710 dated Feb. 22, 2018.
Petersen et al., "Mechanisms for Enlarging Lesion Size During Irrigated Tip Radiofrequency Ablation: Is There a Virtual Electrode Effect?" Journal of Interventional Cardiology, vol. 17, No. 3, pp. 171-177 (2004).
S. Mahapatra, J. Tucker-Schwartz, "Pressure frequency characteristics of the pericardial space and thorax during subxiphoid access for epicardial ventricular tachycardia ablation," Heart Rhythm, vol. 7, No. 5, pp. 604-609, 2010.
Scanavacca et al., "Catheter Ablation of Atrial Fibrillation. Techniques and Results," Arquivos Brasileiros de Cardiologia, vol. 85, No. 4, 7 pps., (2005).
Schwartzman et al., "Catheter Ablation of Ventricular Tachycardia Associated with Remote Myocardial Infarction: Utility of the Atrial Transseptal Approach," Journal of Interventional Cardiac Electrophysiology, vol. 1, pp. 67-71 (1997).
Sosa et al., "Nonsurgical transthoracic epicardial catheter ablation to treat recurrent ventricular tachycardia occuring late after myocardial infarction," J. Am. Coll. Cardiol., vol. 35, No. 6, pp. 1442-1449, 2000.
Sosa, "Epicardial Mapping and Ablation Techniques to Control Ventricular Tachycardia," Journal of Cardiovascular Electrophysiology, 2005, p. 449-452, vol. 16, No. 4.
Tucker-Schwartz et al., "Pressure-Frequency Sensing Subxiphoid Access System for Use in Percutaneous Cardiac Electrophysiology: Prototype Design and Pilot Study Results," IEEE Transactions on Biomedical Engineering, vol. 56, pp. 1160-1168 (May 2009).
Tungjitkusolmun et al., "Finite Element Analyses of Uniform Current Density Electrodes for Radio-Frequency Cardiac Ablation," IEEE Transactions on Biomedical Engineering, vol. 47, No. 1, pp. 32-40, (2000).
Written Opinion of the International Searching Authority corresponding to PCT/US2008/056643 dated Aug. 22, 2008.
Decision to Grant corresponding to European Patent Application No. 08743794.3 dated Jan. 7, 2022.
Grimard et al. (2010) "Percutaneous epicardial radiofrequency ablation of ventricular arrhythmias after failure of endocardial approach: a 9-year experience," J. Cardiovasc. Electrophysiol., vol. 21, No. 1, pp. 56-61.
Intent to Grant corresponding to European Patent Application No. 08743794.3 dated Aug. 27, 2021.
Notice of Allowance corresponding to U.S. Appl. No. 15/295,102 dated Jun. 2, 2022.
Notice of Allowance corresponding to U.S. Appl. No. 15/295,102 dated Sep. 15, 2022.
Notice of Allowance corresponding to U.S. Appl. No. 15/295,102 dated Mar. 2, 2023.
Notice of Allowance corresponding to U.S. Appl. No. 16/236,664 dated Dec. 8, 2022.
Office Action corresponding to U.S. Appl. No. 15/295,102 dated Nov. 18, 2021.
Office Action corresponding to U.S. Appl. No. 16/236,664 dated Feb. 15, 2022.
Sacher et al. (2009) "Prevalence of epicardial scar in patients referred for ventricular tachycardia ablation," Heart Rhythm, vol. 6, pp. S175-S176.
Sosa et al. (1998) "Endocardial and epicardial ablation guided by nonsurgical transthoracic epicardial mapping to treat recurrent ventricular tachycardia," J. Cardiovasc. Electrophysiol., vol. 9, No. 3, pp. 229-239.
Tedrow et al. (2009) "Strategies for epicardial mapping and ablation of ventricular tachycardia," J. Cardiovasc. Electrophysiol., vol. 20, No. 6, pp. 710-713.
Zei et al. (2006) "Epicardial Catheter Mapping and Ablation of Ventricular Tachycardia," Heart Rhythm, vol. 3, pp. 360-363.

* cited by examiner

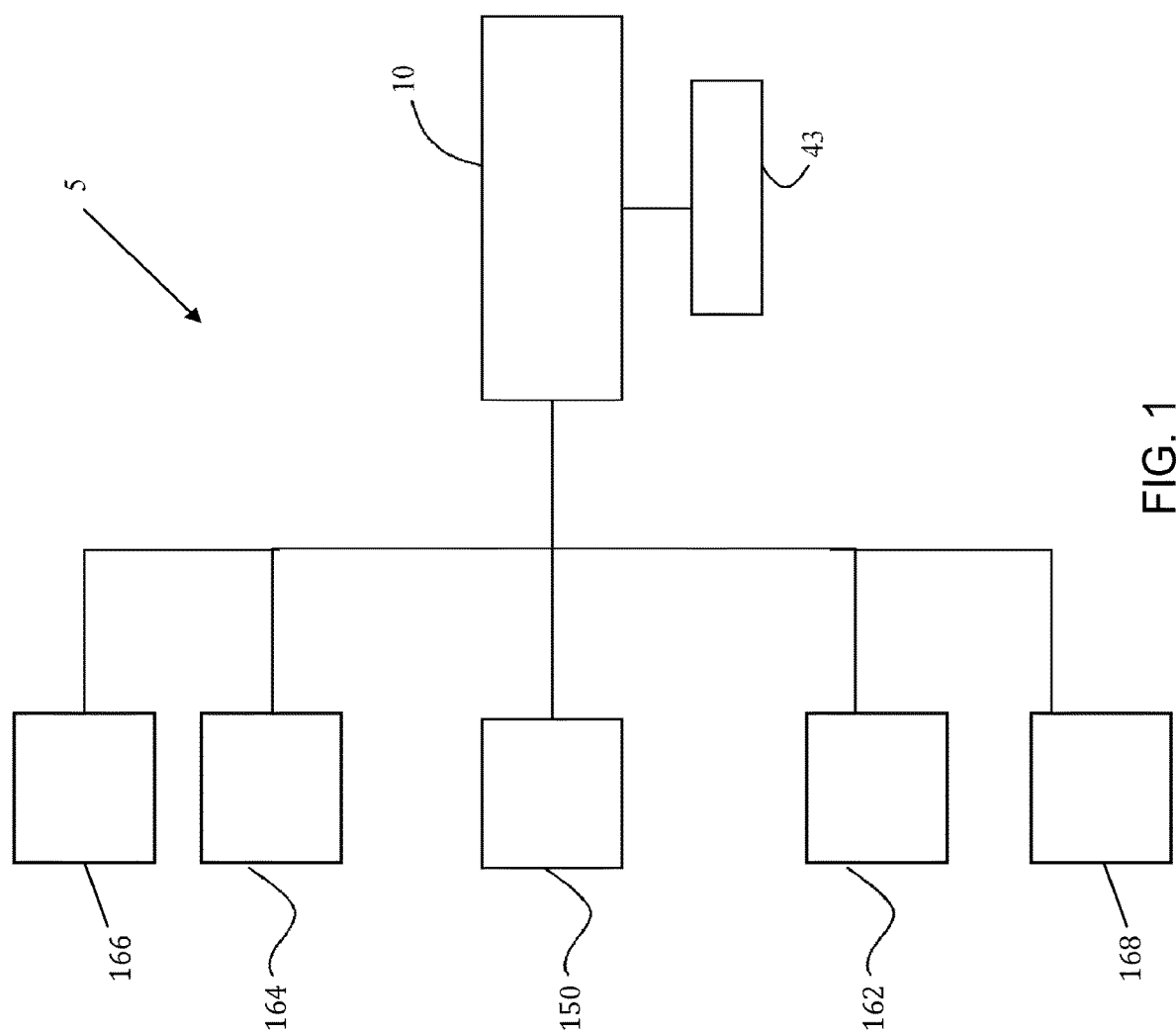

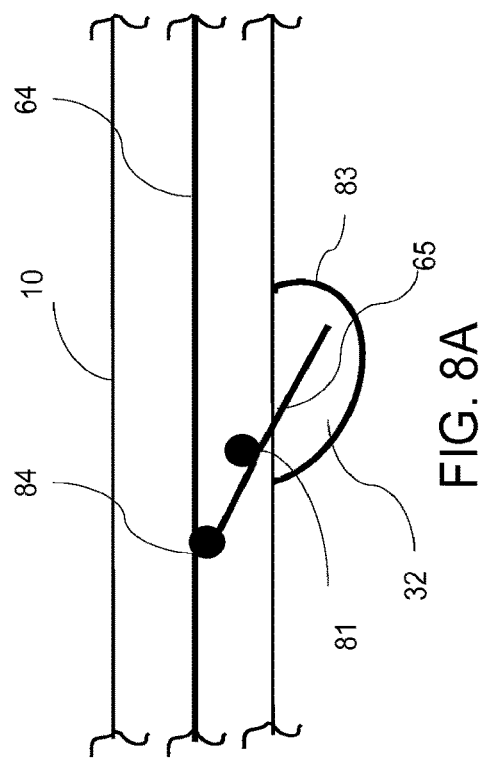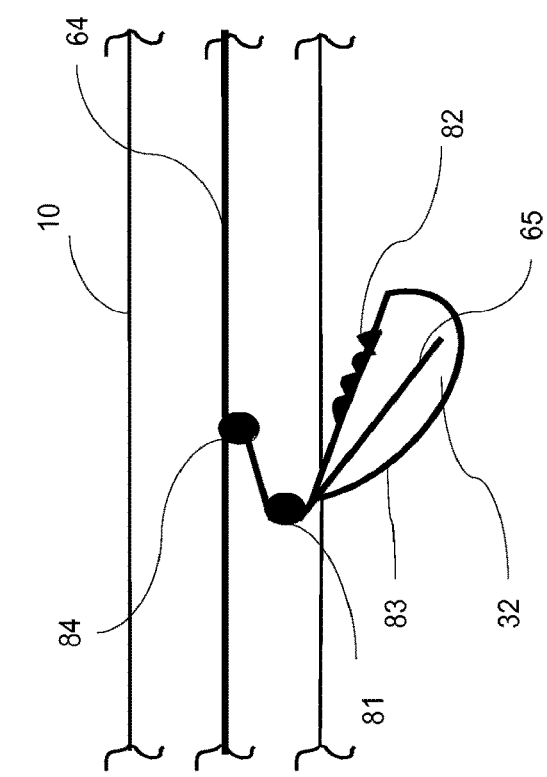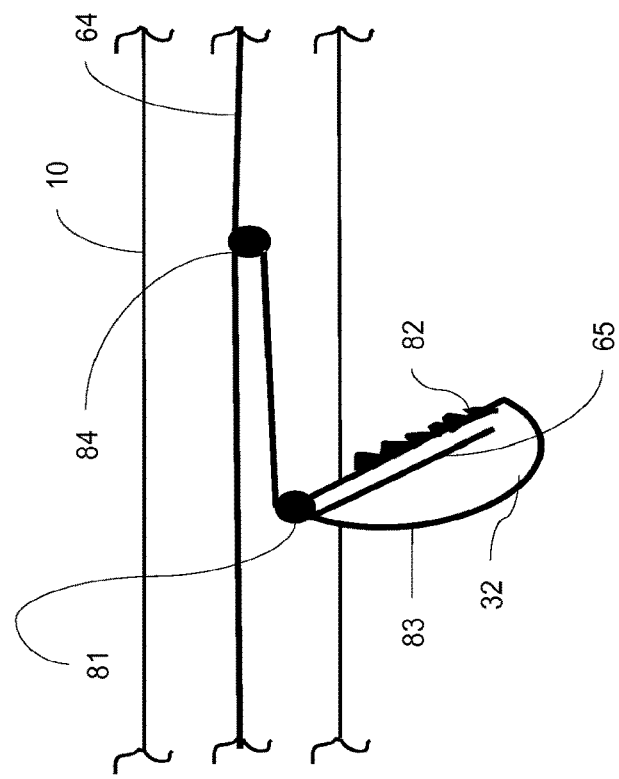

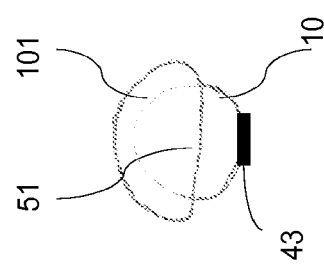
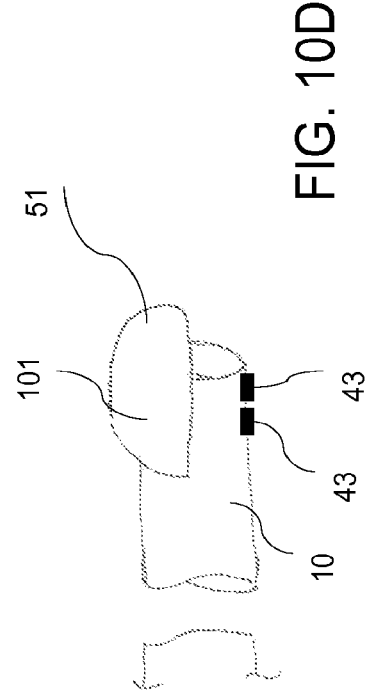

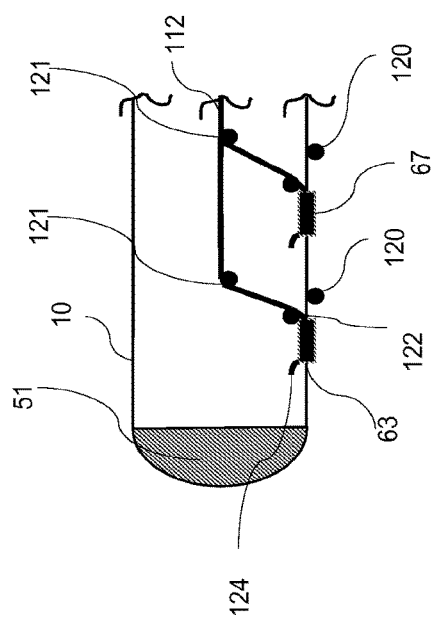
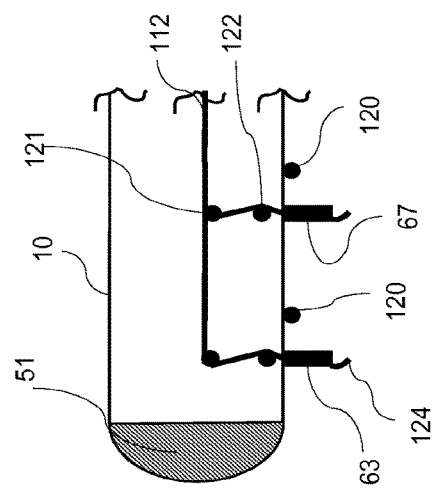

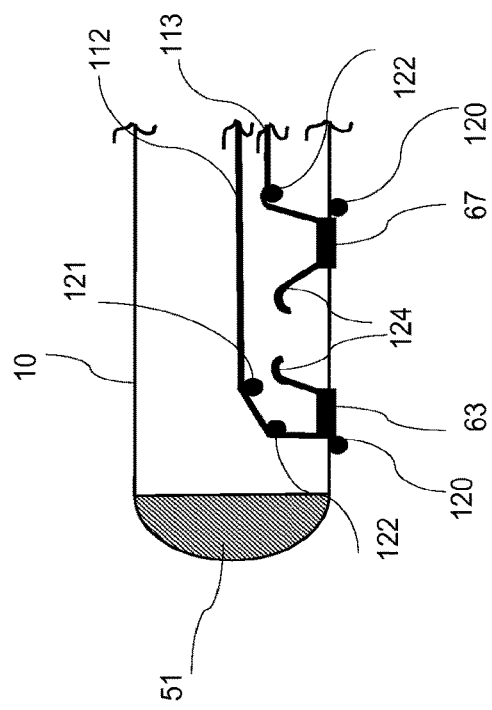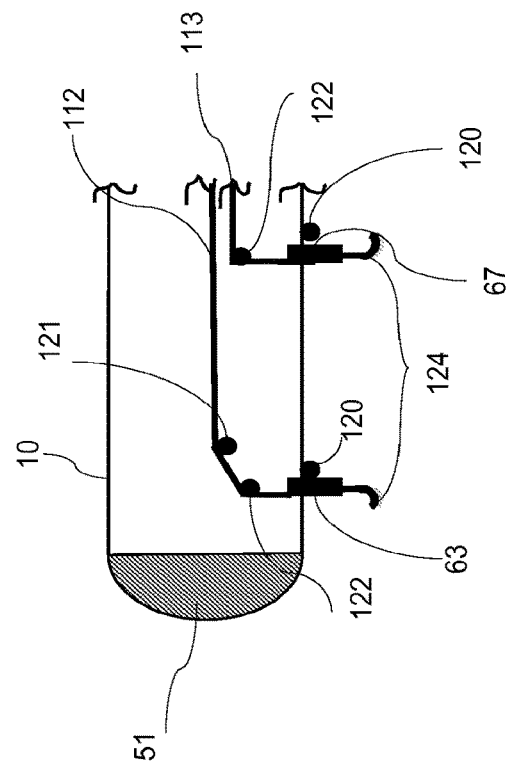

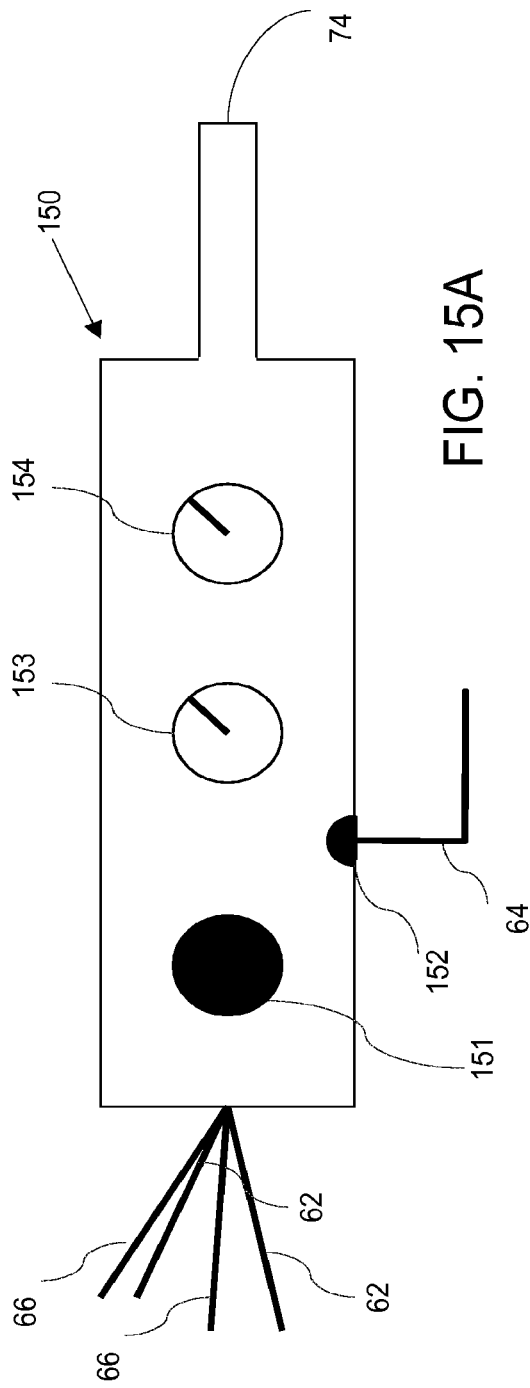
FIG. 15A
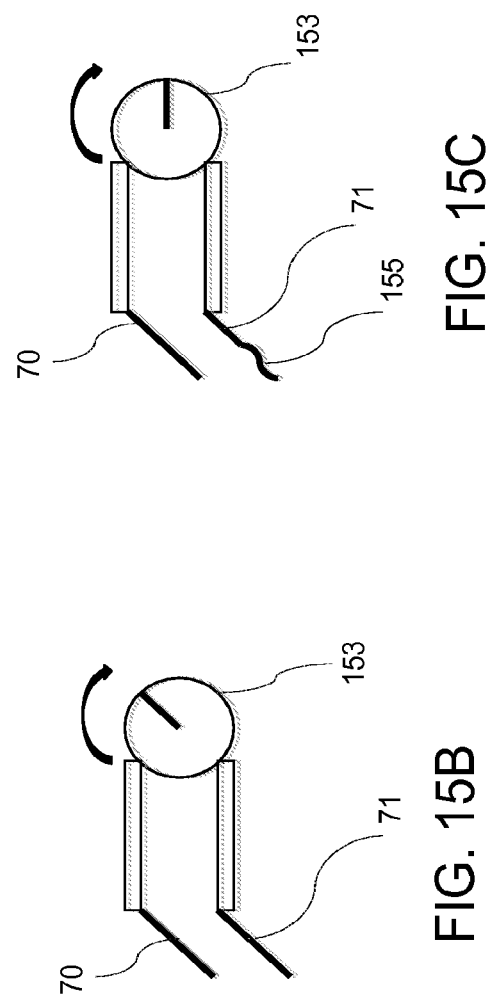
FIG. 15B
FIG. 15C

STEERABLE EPICARDIAL PACING CATHETER SYSTEM PLACED VIA THE SUBXIPHOID PROCESS

RELATED APPLICATIONS

The present application is a continuation of U.S. application Ser. No. 12/741,710, filed May 6, 2010 now abandoned, entitled "Steerable Epicardial Pacing Catheter System Placed via the Subxiphoid Process," which is a National Stage Entry of PCT/US2008/082835, filed Nov. 7, 2008 and claims priority from U.S. Provisional Application Ser. No. 60/986,786, filed Nov. 9, 2007, entitled "Passive Fixation, Steerable Epicardial Lead to be Placed via the Subxiphoid Process for Pacing Left Ventricle, Right Ventricle, Right Atrium and Left Atrium and Cardiac Defibrillation," and U.S. Provisional Application Ser. No. 61/023,727, filed Jan. 25, 2008, entitled "Steerable Epicardial Lead to be Placed via the Subxiphoid Process for Left Ventricular Pacing and Related Method." the disclosures of which are hereby incorporated by reference herein in their entirety.

This application is related to PCT International Application No. Serial No. PCT/US2008/056643, filed Mar. 12, 2008, entitled, "Access Needle Pressure Sensor Device and Method of Use," the disclosure of which is hereby incorporated by reference herein in its entirety.

This application is related to PCT International Application No. Serial No. PCT/US2008/056816, filed Mar. 13, 2008, entitled, "Epicardial Ablation Catheter and Method of Use," the disclosure of which is hereby incorporated by reference herein in its entirety.

This application is related to PCT International Application No. Serial No. PCT/US2008/057626, filed Mar. 20, 2008, entitled, "Electrode Catheter for Ablation Purposes and Related Method Thereof," the disclosure of which is hereby incorporated by reference herein in its entirety.

FIELD OF THE INVENTION

The present technology relates generally to the field of medical devices to be used for cardiological procedures. More specifically, the technology is in the subfield of catheterization devices to be used for epicardial pacing.

BACKGROUND OF THE INVENTION

Congestive heart failure effects between 4 and 5 million people in the United States and accounts for about $15 billion per year in hospitalization costs alone. While medical therapy, such as prescription drugs, may benefit a number of patients, side effects prevent some patients from completing therapy. Moreover, few patients are completely cured of their symptoms.

In recent years simultaneous pacing of both ventricles (via a biventricular pacemaker) has been shown in multiple studies to improve the quality of life and extend survival of such patients. The American College of Cardiology and American Heart Association has, therefore, recommended that all patients having class II, III or IV heart failure with a wide QRS complex (electrocardiograph deflections of the Q, R and S waves) receive a biventricular pacemaker. This recommendation alone encompasses up to one million people per year in the US, and uses for this type of device are expanding.

Unfortunately, due to inherent difficulties in placing left ventricular (LV) leads, less than 15% of eligible patients are able to receive this device. Unlike the RV, the electrical lead can not be placed directly into the LV due to the unacceptably high risk of stroke. The lead must, therefore, be placed on the surface of the LV. In order to accomplish this placement, a lead is threaded through the right atrium (RA) using a venous system, and passed through the coronary sinus (CS) to any of a number of small veins in communication with the surface of the LV.

Quantitative clinical results, especially those reporting the statistics of negative outcomes, are seldom published. However, in procedures conducted at the inventors' high volume university hospital, 20% of patients have been found to have a very difficult access to the CS, resulting in an abandonment of the procedure. In an additional 20% of patients, a vein in communication with an optimal location on the LV can not be found within the CS. As an example, if one is trying to place a lead on the lateral aspect of the LV (an ideal location), but there is no vein extending from within the CS to the lateral aspect of the LV, a lead can not be placed here. Worse still, many of these patients have multiple areas of dead heart tissue, so even if a lead can be placed within a vein, it might not pace the heart. Even moving the lead slightly would help, but the vein acts like a railroad track to limit placement. All of these limitations result in an unpredictable procedure time, making it difficult for hospitals and doctors to plan the operation.

At present, the most effective option to pace the LV is through invasive surgery requiring cardiac surgeons. The newest techniques allow surgeons to either open a patient's chest or cut between the ribs to place the lead anywhere on the LV. Even the most "minimally invasive" leads currently available require a lateral thoracotomy necessitating a surgeon. Both the Ncontact® and Heartlander® tools, which are not designed to pace, require surgical incisions.

There are two significant barriers to widespread application of these surgical techniques. First, surgical procedures are generally more invasive and require longer recovery times. Second, most cardiologists consider it the standard of care to attempt an initial placement of a lead via CS access; only after that fails is surgery considered. To avoid the need for additional surgical intervention, a cardiologist may choose a sub-optimal location for lead placement. This is typically in keeping with the wishes of most patients; minimally invasive techniques are preferred whenever possible.

There is therefore a need in the art whereby one would be able to place a lead for pacing on any optimal site of the LV based solely on what is clinically efficient for the patient and not the heart's anatomy. Moreover, if this could be accomplished by a cardiologist (non-surgeon) without the need for invasive surgery, the procedure would be used more often. Thus, instead of only 15% of patients receiving biventricular pacing, close to 100% of patients could receive it.

The following U.S. patent documents discuss catheterization tools for cardiology: U.S. Pat. No. 7,142,919 to Hine et al.; U.S. Pat. No. 7,130,699 to Huff et al.; U.S. Pat. No. 7,120,504 to Osypka; U.S. Pat. No. 7,101,362 to Vinney; U.S. Pat. No. 7,090,637 to Danitz et al.; U.S. Pat. No. 7,089,063 to Lesh et al.; U.S. Pat. No. 7,059,878 to Hendrixson et al.; U.S. Pat. No. 7,041,099 to Thomas et al.; U.S. Pat. No. 7,027,876 to Casavant et al.; U.S. Pat. No. 7,008,418 to Hall et al.; U.S. Pat. No. 6,973,352 to Tsutsui et al.; U.S. Pat. No. 6,936,040 to Kramm et al.; U.S. Pat. No. 6,921,295 to Sommer et al.; U.S. Pat. No. 6,876,885 to Swoyer et al.; U.S. Pat. No. 6,868,291 to Bonner et al., all of which are incorporated by reference herein in their entirety. No reference discloses the conceptual arrangements for an integrated cardiological device for epicardial pacing.

To overcome these limitations, we have conceived the subject device and method of use, as described in the Summary of the Invention and Detailed Description of the Drawings below.

These and other objects, along with advantages and features of the invention disclosed herein, will be made more apparent from the description, drawings and claims that follow.

SUMMARY OF THE INVENTION

An aspect of an embodiment (or partial embodiment thereof) of the present invention includes an apparatus and means for treating congestive heart failure and arrhythmias (both bradycardias and tachycardias) of the heart. For example, the invention provides for a novel means and method of placing an epicardial lead within a patient for the purpose of permanent multi-site, cardiac pacing and defibrillation, including left ventricular pacing.

An aspect of an embodiment (or partial embodiment thereof) of the present invention includes a lead that paces LV, RV, LA and RA at the same time or in sequence. It could even pace two separate points on the same chamber (the LV or the RV) at the same time or at some offset. This has an important advantage, for example, if a region of tissue ever dies in heart attack, the present invention method can still pace from elsewhere.

An aspect of an embodiment (or partial embodiment thereof) of the present invention may include placing a bipolar pacing lead through a subxiphoid incision and then channeling it back to a pacemaker. The procedure may evolve through three distinct stages. In the earliest stage, one would place the lead on the left ventricle and tunnel it underneath the pectoral muscle back to the chest wall where the pacemaker would normally be placed. In the second, one would place the lead back to the subxiphoid process, attach it to a battery that is positioned just on the outside of the xiphoid process and have it wirelessly communicate with the main pacemaker. Lastly one would place a button-like object right on the top of the left ventricle and then communicate wirelessly back to the main pacemaker. Still yet, another embodiment of the means and method of the invention may include having the battery, anode and cathode means all compounded on the end of the lead so that there would not be any need to have another excision to bring any of the components back out of the heart.

An aspect of an embodiment or partial embodiment of the present invention (or combinations of various embodiments in whole or in part of the present invention) comprises an epicardial pacing system. The system may comprise: an epicardial catheter configured to be disposed in the middle mediastinum of the thorax of a subject for use in electrical pacing of the heart at one or more locations on the epicardial surface. The epicardial pacing catheter comprising: a proximal portion, distal portion, and a longitudinal structure there between; and at least one electrode in communication with the distal portion, wherein the at least one electrode is insulated on at least one side to allow pacing of the heart without damage to adjacent anatomical structures.

An aspect of an embodiment or partial embodiment of the present invention (or combinations of various embodiments in whole or in part of the present invention) comprises a method for use with an epicardial pacing catheter. The method may comprise: disposing the epicardial pacing catheter in the middle mediastinum of the thorax of a subject; and pacing the heart at one or more locations with electrical energy from an at least one electrode; and at least partially insulating the electrical energy to allow pacing of the heart without damage to adjacent anatomical structures.

The epicardial pacing system and related method includes an epicardial catheter configured to be disposed in the middle mediastinum of the thorax of a subject for use in electrical pacing (and/or other diagnostic or therapeutic procedure) of the heart at one or more locations on the epicardial surface. The epicardial pacing catheter may include at least one electrode whereby the electrode is insulated on at least one side to allow pacing of the heart without damage to adjacent anatomical structures.

These and other objects, along with advantages and features of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 1 schematically illustrates the overall configuration of the epicardial pacing catheter system.

FIGS. 8(A)-(C) schematically illustrate cross-sectional views of an example embodiment further comprising a stabilization means for stabilizing the example embodiment. The stabilization means illustrated in an un-deployed position, partially deployed position, and deployed position, respectively.

FIG. 10(C) schematically illustrates an axial view of an exemplary embodiment of the epicardial pacing catheter looking at the distal tip of the insulating hood.

FIG. 10(D) schematically illustrates a perspective view of an exemplary embodiment of the epicardial pacing catheter.

FIG. 12(A) schematically illustrates a cross section of an exemplary embodiment of the epicardial pacing catheter comprising a deployable anode and cathode in an un-deployed state.

FIG. 12(B) schematically illustrates a cross section of an exemplary embodiment of the epicardial pacing catheter comprising a deployable anode and cathode in a fully-deployed state.

FIG. 14(A) schematically illustrates a cross section of an exemplary embodiment of the epicardial pacing catheter comprising a deployable anode and cathode in an un-deployed state.

FIG. 14(B) schematically illustrates a cross section of an exemplary embodiment of the epicardial pacing catheter comprising a deployable anode and cathode in a fully-deployed state.

FIG. 15(A) schematically illustrates an example embodiment of an external control handle.

FIG. 15(B) schematically illustrates an example embodiment of the proximal steering control means or a least part of the steering control means integral to the control handle.

FIG. 15(C) schematically illustrates an example embodiment wherein the proximal steering control means or a least part of the steering control means integral to the control handle has been activated.

DETAILED DESCRIPTION OF THE DRAWINGS

Figures 2A, 2B:
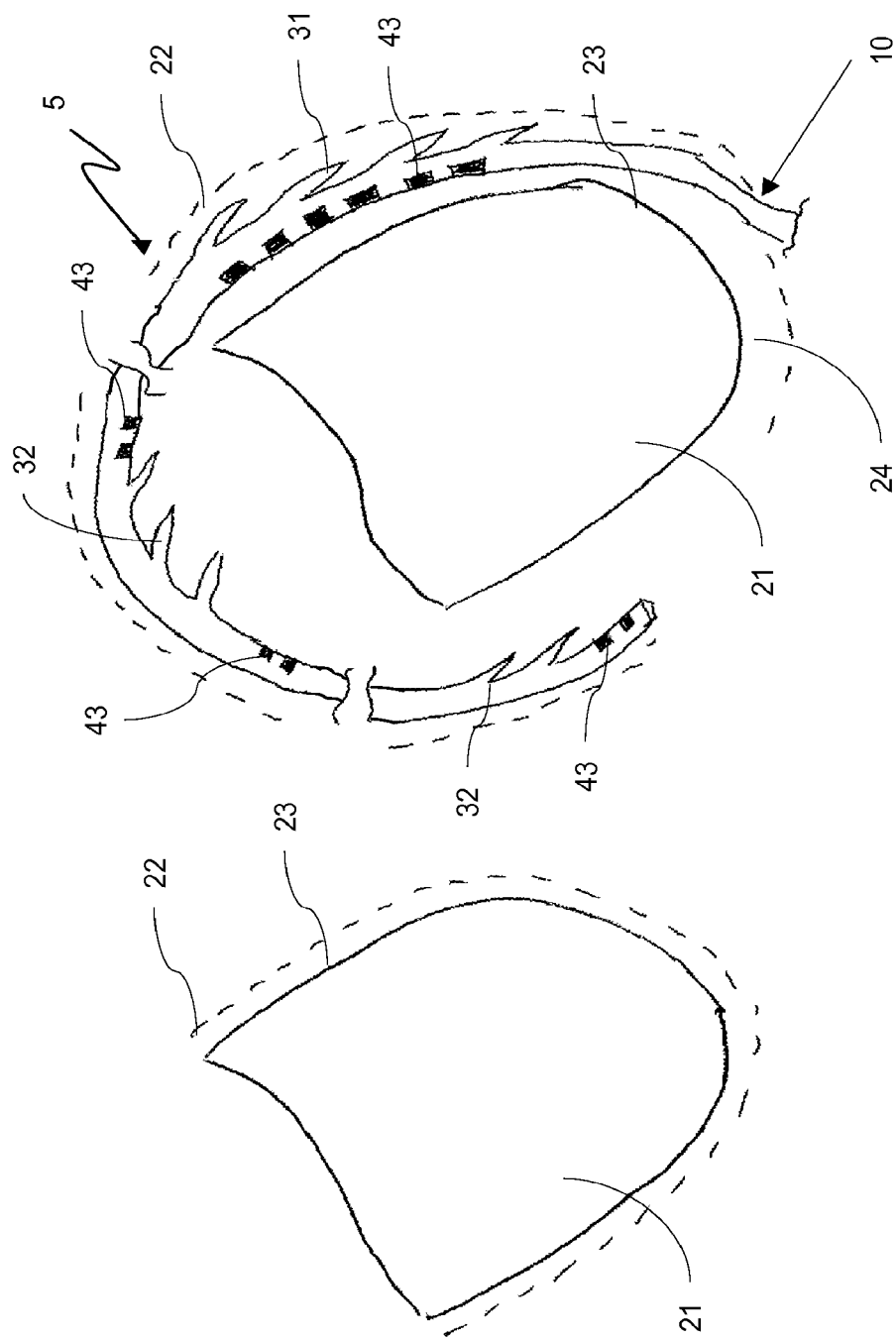
FIG. 2 schematically illustrates the pericardium and heart alone (FIG. 2(A)) and an example embodiment in position relative to the heart (FIG. 2(B)).

The following detailed description is of the best presently contemplated modes of carrying out the invention. This description to be taken in a limiting sense, but is made merely for the purpose of illustrating general principles of embodiments of the invention.

FIG. 1 schematically illustrates an overview of an exemplary embodiment of the epicardial pacing system 5 comprising an epicardial pacing catheter 10 in communication with at least one electrode 43, a control means or control handle 150, an interface member 162, a processor 164 or computer, power supply 166 or battery, or voice control instrumentation/system 168.

The control means 150 may be in communication with the proximal portion of the catheter 10, wherein the control means 150 is controllably connected to at least one electrode 43. In one embodiment, the control means may be a control handle or controller as desired or required. In another embodiment, the control handle (or control means) may be removable. The epicardial pacing catheter 10 may further comprises a processor 164 or computer. The processor 164 may be in communication with said epicardial pacing catheter 10 and system. The processor 164 may be located at or near the patient's shoulder, for example. The epicardial pacing catheter 10 further comprises an interface member 162 in communication with said epicardial pacing catheter 10. The interface member 162 may be in remote and/or local communication with the processor 164, pacing system 5, catheter 10, controller 150, power supply 166, and/or voice control instrumentation to provide information to and/or from a patient, physician, technician, or a clinician. Further, any of the components and systems illustrated in FIG. 1 may be in communication with each other, as well as other systems, computers, devices, printers, displays, PDAs, networks, memory storage, and voice control instrumentations as desired or required.

As discussed, the epicardial pacing system 5 may comprise a power supply 166. The power supply 166 may comprise a small battery located at the subxiphoid area, preferably of a silicone silver-gallium kind designed specifically for use in implantable cardiac defibrillators (ICDs). The power characteristics of the particular battery may be such that it can maintain the same voltage for a long period of time before falling off suddenly.

The epicardial pacing system 5 and epicardial pacing catheter 10 may further comprise a wireless communication system, wherein the processor 164, power supply 166, voice control instrumentation 168, interface member 162 or desired components of the system 5 may be wirelessly connected to one another. In another embodiment, the battery and processor 164 are both located in the subxiphoid area.

It should be appreciated that any of the components or modules referred to with regards to any of the present technology embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardwares.

Next, as will be illustrated in Figures that follow, the epicardial pacing catheter 10 in accordance with the present technology may comprise a proximal portion, a distal portion, and a longitudinal structure there between. It should be appreciated that the distal portion may be considered at the distal end tip of the epicardial pacing catheter 10; or a portion or segment at or in the vicinity of the distal end tip of the epicardial pacing catheter 10 or a portion or segment leading up to (or partially up to but not all the way up to) the distal end of the catheter 10 as desired or required. The length and location of the distal portion may vary as desired or required in order to practice the technology according to medical procedures and anatomical considerations.

It should also be appreciated that the proximal portion may be considered the tip of the beginning of the catheter 10; or a portion or segment at or in the vicinity of the proximal end of the catheter 10 or a portion or segment leading up to (or partially up to but not all the way up to) the proximal end of the catheter 10 as desired or required. The length and location of the proximal portion may vary as desired or required in order to practice the technology according to medical procedures and anatomical considerations.

The proximal portion, distal portion and longitudinal structure there between may be integrally formed from a biocompatible material having requisite strength and flexibility for deployment within a patient. The proximal portion, distal portion, and longitudinal structure there between may have a lubricious outer surface comprising a material having a low coefficient of friction, such as, but not limited to, silicone, polyurethane, or Teflon, or combination thereof. The proximal portion, distal portion, and longitudinal structure there between may further have an outer surface comprising a drug eluting surface and/or a surface impregnated with sirilimus to prevent the production of fibrosis within a patient. The longitudinal structure may be between about 15 cm and about 100 cm in length, and between about 2 mm and about 6 mm in diameter. It should be appreciated that the length of the longitudinal structure may be longer or shorter as may be desired or required according to medical procedures, device/system operations and anatomical considerations. The cross section of the longitudinal structure comprises an oval, circle, ellipse, polygon, or semi-circular shape. The longitudinal structure may be any one of: lumen, conduit, channel, passage, pip, tunnel or bounded tubular surface.

The epicardial pacing catheter 10 further comprises at least one electrode 43 in communication with the distal portion, wherein the at least one electrode 43 is insulated on at least one side to allow pacing of the heart without damage to adjacent structures.

The at least one electrode 43 may be constructed of platinum, gold, silver, iridium, or any alloy thereof, or other conducting materials known in the art. The at least one electrode 43 may comprise a roughened, profiled, or otherwise prepared surface to increase the total surface area for energy transmission. The at least one electrode 43 may be semi-cylindrical or arc-like in shape, and may be contoured to be compatible with proximate anatomical structures. The at least one electrode 43 may be between about 0.3 mm and about 4 mm in length, and may be spaced between about 1 mm and about 25 mm from each other. Further, the at least one electrode 43 may be a pair of electrodes, commonly referred to as an anode and cathode in the art. Finally, the at least one electrode 43 may be deployable. It should be appreciated that the length of the electrodes may be longer or shorter as may be desired or required according to medical procedures, device/system operations and anatomical considerations.

It should be appreciated that the various sheaths, catheters and guidewires, or any related components disclosed herein, may have a circular or oval-shaped cross-section or various combinations thereof. Further, it should be appreciated that various sheaths, catheters and guidewires, or any related components disclosed herein may have any variety of cross sections as desired or required for the medical procedure or anatomy.

Moreover, it should be appreciated that any of the components or modules referred to with regards to any of the present invention embodiments discussed herein, may be a variety of materials and/or composites as necessary or required. Still further, it should be appreciated that any of the components or modules (or combination thereof) may provide shape, size and volume contoured by adjusting its geometry and flexibility/rigidity according to the target location or anatomy (or region, including structure and morphology of any location) being treated.

FIG. 2(A) schematically illustrates the pericardium and heart alone. The pericardium 22 is shown in close proximity to the epicardium 23.

FIG. 2(B) schematically illustrates three contiguous sections of an example embodiment implanted around the heart 21. The epicardial pacing catheter 10 of the epicardial pacing system 5 is positioned in the pericardial space, cavity or sack 24, or the area between the pericardium 22 and epicardium 23. All of the electrodes 43 are facing the heart 21. The epicardial pacing catheter 10 further comprises outward facing bumper tabs 31 and inward facing friction tabs 32 to stabilize the epicardial pacing catheter 10 from moving within the pericardial sack 24, once it is implanted.

Although not shown, an aspect of an embodiment of the present technology may be implemented with an access needle (introducer needle), conduit or the like. The access needle or conduit is adapted to be inserted into the epicardial region or other body part or body space so as to provide an access or guideway for the epicardial pacing catheter 10. An example of an access system is disclosed in PCT International Application No. Serial No. PCT/US2008/056643, filed Mar. 12, 2008, entitled, "Access Needle Pressure Sensor Device and Method of Use," of which is hereby incorporated by reference herein in its entirety. See for example, but not limited thereto, FIGS. 2 and 5 of the '056643 PCT Application. The access needle sensor device or the like serves as a guideway for introducing other devices into the pericardium 22, for instance, sheath catheters that might subsequently be employed for procedures within the pericardium 22 or other applicable regions, space or anatomy. Other devices that the access device may accommodate with the practice of this invention include, but are not limited thereto, the following: ablation catheters, guide wires, other catheters, visualization and recording devices, drugs, and drug delivery devices, lumens, steering devices or systems, drug or cell delivery catheters, fiber endoscopes, suctioning devices, irrigation devices, electrode catheters, needles, optical fiber sensors, sources of illumination, vital signs sensors, and the like. These devices may be deployed for procedures in an integral body part or space.

It should be appreciated that any data, feedback, readings, or communication from the system (for example, catheters, access needles, sensors, systems, etc.) may be received by the user, clinician, physician, or technician or the like by visual graphics, audible signals (such as voice or tones, for example) or any combination thereof. Additionally, the data, feedback, or communication may be reduced to hard copy (e.g., paper) or computer storage medium. It should be appreciated that the pressure related readings and data may be transmitted not only locally, but remotely as well.

Moreover, an aspect of the invention may be in the field of voice control over medical systems and devices of use in specialized electrophysiology procedures that employ subxiphoid access for the purpose of navigating an interventional or surgical probe onto the epicardial surface of the heart, via pericardial transit. In its most particular form, the invention may be in the specialized category of voice control over instruments and systems that measure the intrathoracic and intrapericardial pressures during the process of navigating said intrathoracic or surgical probe within the patient following subxiphoid insertion.

An aspect of an embodiment or partial embodiment of the subject invention (or combinations of various embodiments in whole or in part of the present invention) is one of providing the working electrophysiologist with a means and method for controlling the operational parameters (e.g., the display functions) of diagnostic and therapeutic cardiological equipment by voice, thus eliminating either the need to temporarily take their hands off the patient or the need to have an additional EP Lab technician available to perform such tasks. (Such personnel are often needed to insure that the clinician need never touch anything outside the sterile field.). Generally, examples of voice control instrumentation that teach applications in medical applications but not in electrophysiological approaches to cardiological problems include U.S. Pat. Nos. 7,286,992; 7,259,906; 7,247,139; 6,968,223; 6,278,975; 5,970,457; 5,812,978; 5,544,654 and 5,335,313, all of which are hereby incorporated by reference in their entirety.

Additionally, present invention system and method may further comprise imaging said the access needle and the epicardial pacing system (and components thereof) with at least one of magnetic resonance imaging, computed tomography, fluoroscopy, or other radiological modalities. In some embodiments, readings are provided from said sensing of pressure for navigating said needle access and the epicardial pacing system (and components thereof).

Although not shown, as mentioned above, the deploying of the epicardial pacing catheter 10 into the pericardial sack 24 may be minimally invasive, non-surgical, and/or interventional. The deploying of the epicardial pacing catheter 10 may be performed by a non-surgeon and/or cardiologist through use of an access needle and subsequent passage of a guidewire. The access needle may first be inserted through the chest and into the pericardium 22, with the guidewire then put in place. The epicardial pacing catheter 10 may then be coaxially slid over the guidewire to access the pericardial sack 24.

Although not shown and involving another approach, the insertion of a sheath into the pericardial sack 24 may be aided by the use of an access needle and subsequent passage of a guidewire. The access needle may first be inserted into the epicardium, with the guidewire then put in place. The sheath may then be coaxially slid over the guidewire to access the pericardial sack 24. After positioning the sheath in the desired location, the epicardial pacing catheter 10 may then be inserted through the sheath to reach the epicardium 23.

For example, the guideway provides coaxial alignment for the at least one of guide wire, sheath or catheter, which can be inside or outside the needle. The at least one guide wire, sheath, or catheter can also be coaxially aligned with one another. Further, multiple lumens may be implement and configured between the plurality of distal apertures and plurality proximal apertures. It should be appreciated that coaxial alignment does not need to be exact, but rather one conduit, lumen, sheath, or guidewire slid outside or inside of another.

For example, with the present technology, an epicardial access needle-stick may be implemented in the subxiphoid area of the chest and the epicardial pacing catheter 10 only need be advanced a short distance to get to the heart 21. However, it may immediately be steered though an acute angle to avoid the heart itself. Because of this, aspects of the present invention devices and those used in conventional techniques can be contrasted. For instance, conventional endocardial catheters may typically be up to 100 cm in length or longer since they must go from the shoulder to the heart, while an embodiment of the present technology could be, for example, about 20 cm or less since it may only need to go from the chest to the heart. It should be appreciated that the length may be greater than about 20 cm as well. It should be appreciated that the length of the present invention catheter may be longer or shorter as may be desired or required according to medical procedures, device/system operations and anatomical considerations.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g. rat, dog, pig, monkey), etc. It should be appreciated that the subject may be any applicable human patient.

Figure 3:
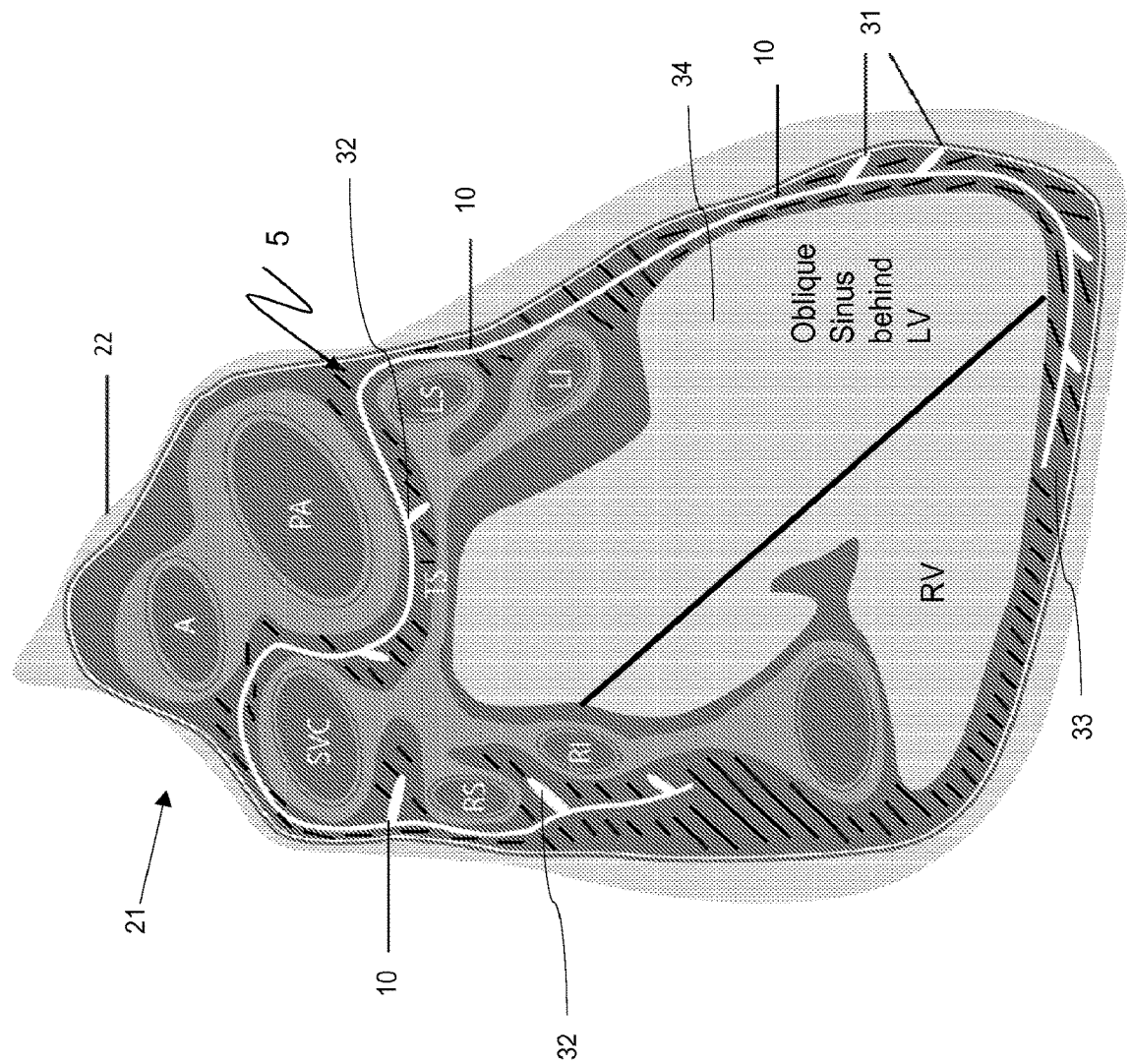
FIG. 3 schematically illustrates an example embodiment passively disposed within the pericardial sack of the heart.

FIG. 3 schematically illustrates an example embodiment of the epicardial pacing catheter 10 of the epicardial pacing system 5 passively disposed within the pericardial sack 24 (shown with hash marks) of the heart 21. A cross section of the heart is shown, revealing critical internal structures, including various great vessels. The epicardial pacing catheter 10 may be used to pace the left ventricle, right ventricle, right atrium, and left atrium. It should be appreciated that the present technology may be used to pace the left ventricle, left atrium, right atrium, right ventricle and/or any combination thereof. The epicardial pacing catheter 10 may first be inserted into the pericardium 22 at the insertion point 33, which may be located at an anterior portion (towards the sternum) of the pericardium 22, adjacent to the left ventricle. The catheter is then advanced posteriorly (towards the spine) within the pericardial sack 24 towards the left atrium, right atrium and transverse sinus. The catheter is further advanced around the posterior of the heart, and pushed anteriorly toward the right ventricle. Once the catheter is in contact with the left ventricle, right ventricle, right atrium and left atrium, a deployable stabilization means may be deployed. Both outward facing bumper tabs 31 and inward facing friction tabs 32 are shown, and prevent the catheter from moving or slipping. The inward facing friction tabs 32 may interact with the outside wall of structures such as, but not limited to, the transverse sinus, superior vena cava, right inferior pulmonary vein, and the right superior pulmonary vein to prevent the catheter from dislodging. The outward facing bumper tabs 31 may push on the pericardium to further secure the catheter 10 against the epicardium (for example, as shown in FIG. 2).

Figure 4C:
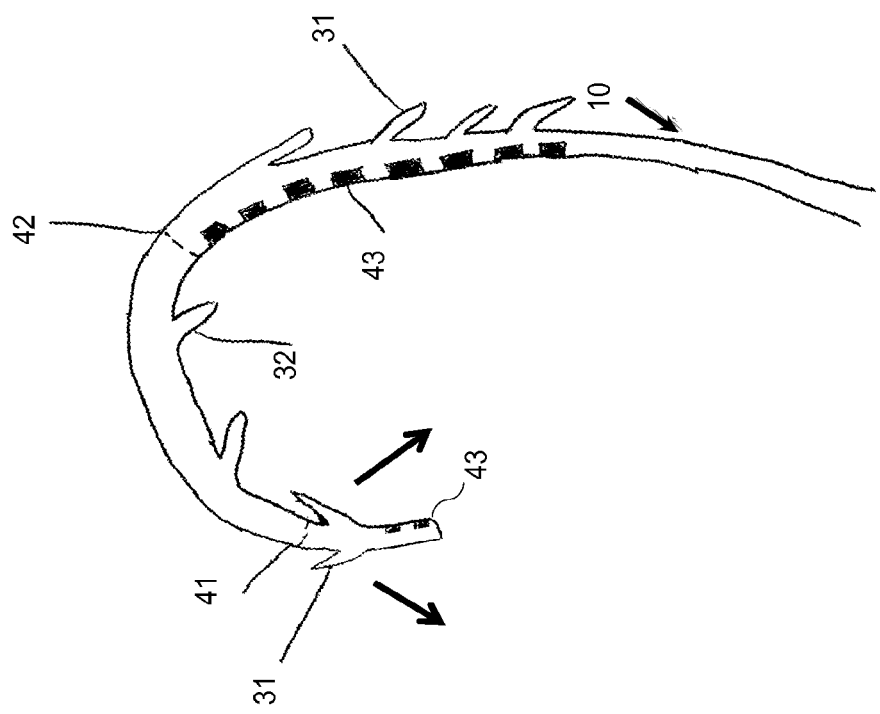
FIGS. 4(A)-(C) schematically illustrate a number of exemplary embodiments of the steering means employed to position the distal portion of an exemplary embodiment of the epicardial pacing catheter in un-tensioned, partial steering, and full steering modes, respectively.
Figure 4B:
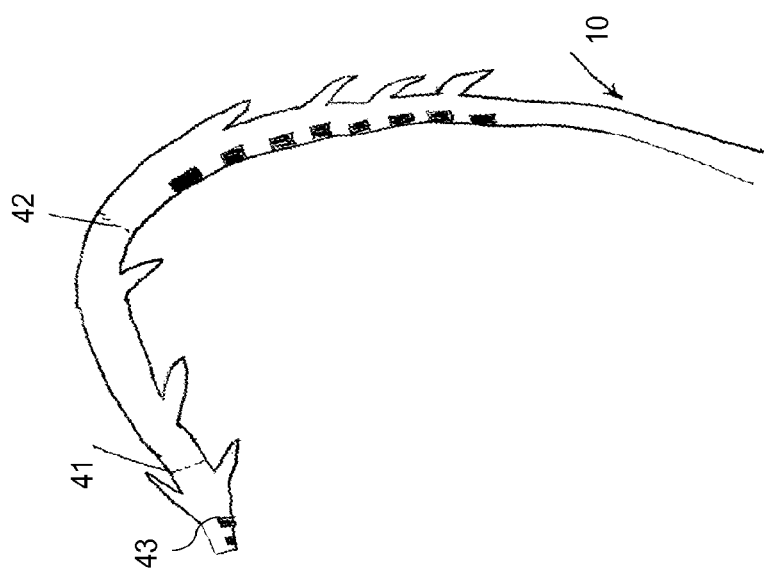
Figure 4A:

FIGS. 4(A)-(C) provide schematic illustrations of some of the operational aspects of an exemplary embodiment of the steering means, system or device associated with the epicardial pacing catheter 10 of the epicardial pacing system. The epicardial pacing catheter 10 further comprises a distal steering means (not shown) and a proximal steering means (not shown) which may have the steering characteristics taught by Mahapatra et al. in PCT International Application No. PCT/US2008/056816, filed Mar. 13, 2008, entitled, "Epicardial Ablation Catheter and Method of Use," hereby incorporated by reference herein in its entirety. The steering means may comprise guidewires, tensioning lines, pull strings, digitating distal tips, magnetic guidance means, wires, rods, chains, bands, chords, ropes, string tubes, filaments, threads, fibers, strands, other extended elements, or any other method known in the art.

For instance, referring to FIGS. 4(A)-(C) of '056816 PCT International Application, there is provided the mechanism of action for obtaining bi-directional steering of the distal tip or portion that may be implemented for the present invention via tensioning or steering means whereby the tip or end is straight, towards the left, and towards the right, respectively.

Figure 7B:
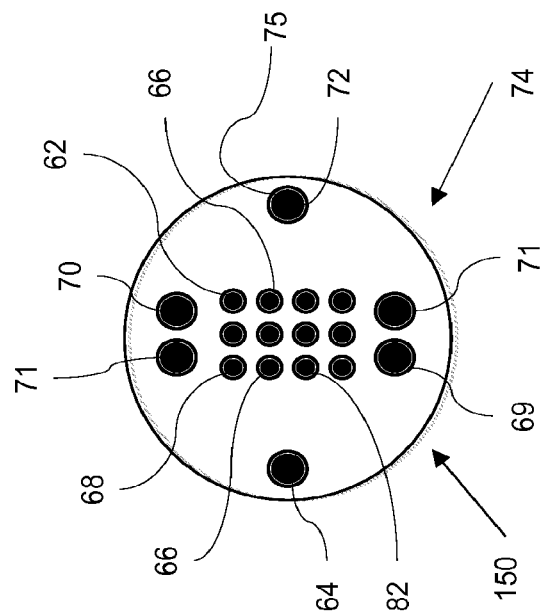
FIGS. 7(A) and (B) schematically illustrate cross sectional views of an exemplary embodiment of the most proximal portion of an exemplary embodiment of the epicardial pacing catheter and the most distal portion of an exemplary embodiment of the control means, respectively.
Figure 7A:
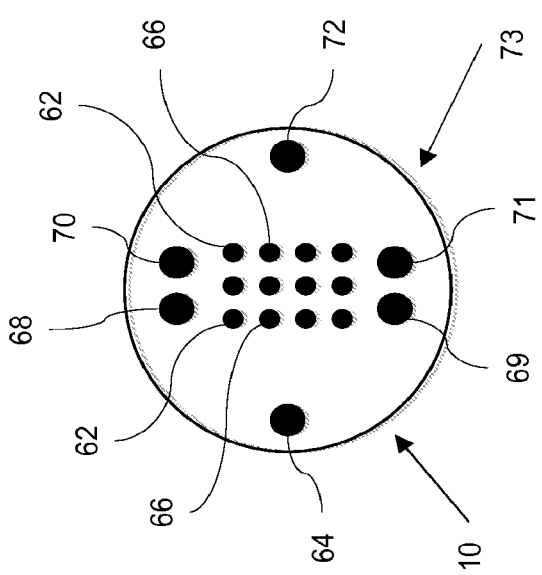

Moreover, for instance and referring to FIGS. 7(A)-7(B) of '056816 PCT International Application there is provided some details of an exemplary mechanism of action for directional steering of the proximal segment of the device that may be implemented for the present technology.

Steering adjustments are made along the proximal point of curvature 42 and distal point of curvature 41 using the proximal steering means (as shown in FIG. 15(B)) and distal steering means (not shown) respectively. The proximal point of curvature 42 may be located between about 1 cm and about 25 cm from the proximal end and the distal point of curvature 41 may be located between about 1 cm and about 20 cm from the distal end. It should be appreciated that the proximal and distal points of curvature may be located at other longer or shorter points and may be implemented as may be desired or required according to medical procedures, device/system operations and anatomical considerations. The steering means are used to direct the epicardial pacing catheter 10 through or navigate it within a patient's body. It should be noted that, while two steering means and points of curvature are shown, the epicardial pacing catheter 10 may further comprise a third and fourth steering means for steering the epicardial pacing catheter 10 around a third and fourth point of curvature. Moreover, though a bi-directional distal point of curvature 41 is shown, it should be appreciated that all points of curvature may be uni-directional, bi-direction, tri-direction, quadra-directional, or greater than quadra-directional.

Specifically, FIG. 4(A) shows an embodiment of the epicardial pacing catheter 10 in the non-deflected state. FIG. 4(B) shows the epicardial pacing catheter 10 in a partially-deflected state. FIG. 4(C) shows the epicardial pacing catheter 10 in a fully-deflected state, as would be the case when it has been navigated into the pericardial space of a subject's heart, or other space or structure. In the fully-deflected state, the at least one electrode 43 is held against a patient's heart by the stabilization means, shown as the inward facing friction tabs 32 and outward facing bumper tabs 31.

The devices, systems, compositions and methods of various embodiments of the invention disclosed herein may utilize aspects disclosed in the following references, applications, publications and patents. Similarly, the steering means, actuator means (as will be discussed below) and navigation means of the various embodiments of the invention disclosed herein may utilize aspects disclosed in the following references, applications, publications and patents, and which are hereby incorporated by reference herein in their entirety:

1. U.S. Patent Application Publication No. 20050251094, Nov. 10, 2005, "System and method for accessing the coronary sinus to facilitate insertion of pacing leads", Peterson, Eric D.

2. U.S Patent Application Publication No. 20040147826, Jul. 29, 2004, "System and method for accessing the coronary sinus to facilitate insertion of pacing leads", Peterson, Eric D.

3. U.S. Pat. No. 6,928,313, Aug. 9, 2005, "System and method for accessing the coronary sinus to facilitate insertion of pacing leads", Peterson, Eric D.

4. U.S. Pat. No. 7,004,937, Feb. 28, 2006, "Wire reinforced articulation segment", Lentz, David J., et al.

5. U.S. Patent Application Publication No. 20040024413, Feb. 5, 2004, "Wire reinforced articulation segment", Lentz, David J., et al.

6. U.S. Patent Application Publication No. 20060064056, Mar. 23, 2006, "Guiding catheter assembly for embolic protection by proximal occlusion", Coyle, James, et al.

7. U.S. Patent Application Publication No. 20030181855, Sep. 25, 2003, "Pre-shaped catheter with proximal articulation and pre-formed distal end", Simpson, John A., et al.

8. U.S. Pat. No. 6,869,414, Mar. 22, 2005, "Pre-shaped catheter with proximal articulation and pre-formed distal end", Simpson, John A., et al.

9. U.S. Patent Application Publication No. 20080262432, Oct. 23, 2008, "System and method for manipulating a guidewire through a catheter", Miller, Sean.

10. U.S. Patent Application Publication No. 20070016068, Jan. 18, 2007, "Ultrasound methods of positioning guided vascular access devices in the venous system", Grunwald, Sorin, et al.

11. U.S. Patent Application Publication No. 20070016070, Jan. 18, 2007, "Endovascular access and guidance system utilizing divergent beam ultrasound", Grunwald, Sorin, et al.

12. U.S. Patent Application Publication No. 20070016072, Jan. 18, 2007, "Endovenous access and guidance system utilizing non-image based ultrasound", Grunwald, Sorin, et al.

13. U.S. Pat. No. 5,916,194, Jun. 29, 1999, "Catheter/guide wire steering apparatus and method", Jacobsen, Stephen C., et al. 14. U.S. Patent Application Publication No. 20070016069, Jan. 18, 2007, "Ultrasound sensor", Grunwald, Sorin, et al.

15. U.S. Pat. No. 6,500,130, Dec. 31, 2002, "Steerable guidewire", Kinsella, Bryan, et al.

16. U.S. Patent Application Publication No. 20020082523, Jun. 27, 2002, Steerable guidewire", Kinsella, Bryan, et al. . . . .

17. U.S. Patent Application Publication No. 20060025705, Feb. 2, 2006, "Method for use of vascular guidewire", Whittaker, David R., et al.

18. U.S. Patent Application Publication No. 20050020914, Jan. 27, 2005, "Coronary sinus access catheter with forward-imaging", Amundson, David, et al.

19. U.S. Patent Application Publication No. 20040034365, Feb. 19, 2004, "Catheter having articulation system", Lentz, David J., et al.

20. U.S. Patent Application Publication No. 20060064058, Mar. 23, 2006, "Guiding catheter with embolic protection by proximal occlusion", Coyle, James.

21. U.S. Patent Application No. 20080097399, "Catheter with adjustable stiffness, Sachar, Ravish, et al.

22. U.S. Patent Application Publication No. 20080051671, Feb. 28, 2008, "Intravascular filter monitoring", Broome, Thomas E., et al.

23. U.S. Pat. No. 6,616,676, Sep. 9, 2003, "Devices and methods for removing occlusions in vessels", Bashiri, Mehran, et al.

24. U.S. Patent Application Publication No. 20020072737, Jun. 13, 2002, "System and method for placing a medical electrical lead", Belden, Elisabeth L., et al.

25. U.S. Pat. No. 7,004,937, Feb. 28, 2006, "Wire reinforced articulation segment", Lentz, David J., et al.

26. U.S. Patent Application Publication No. 20040024413, Feb. 5, 2004, "Wire reinforced articulation segment", Lentz, David J, et al.

27. U.S. Patent Application Publication No. 20060064056, Mar. 23, 2006, "Guiding catheter assembly for embolic protection by proximal occlusion", Coyle, James, et al.

27. U.S. Pat. No. 6,869,414, Mar. 22, 2005, "Pre-shaped catheter with proximal articulation and pre-formed distal end", Simpson, John A., et al.

28. U.S. Patent Application Publication No. 20070016068, Jan. 18, 2007, "Ultrasound methods of positioning guided vascular access devices in the venous system", Grunwald, Sorin, et al.

28. U.S. Patent Application Publication No. 20070016070, "Endovascular access and guidance system utilizing divergent beam ultrasound", Grunwald, Sorin, et al.

29. U.S. Patent Application Publication No. 20070016072, "Endovenous access and guidance system utilizing non-image based ultrasound", Grunwald, Sorin, et al 30. U.S. Patent Application Publication No. 20080262432, Oct. 23, 2008, "System and method for manipulating a guidewire through a catheter", Miller, Sean.

31. U.S. Patent Application Publication No. 20070016069, Jan. 18, 2007, "Ultrasound sensor", Grunwald, Sorin.

32. U.S. Patent Application Publication No. 20060025705, Feb. 2, 2006, "Method for use of vascular guidewire", Whittaker, David R., et al.

33. U.S. Patent Application Publication No. 20030181855, Sep. 25, 2003, "Pre-shaped catheter with proximal articulation and pre-formed distal end", Simpson, John A., et al.

34. U.S. Patent Application Publication No. 20050020914, Jan. 27, 2005, "Coronary sinus access catheter with forward-imaging", Amundson, David, et al.

35. U.S. Pat. No. 5,916,194, Jun. 29, 1999, "Catheter/guide wire steering apparatus and method", Jacobsen, Stephen C., et al.

36. U.S. Patent Application Publication No. 20060064058, Mar. 23, 2006, "Guiding catheter with embolic protection by proximal occlusion", Coyle, James.

37. U.S. Patent Application Publication No. 20040186507, Sep. 23, 2004, "Stent delivery system and method of use", Hall, Todd A., et al.

38. U.S. Patent Application Publication No. 20050027243, Feb. 3, 2005, "Steerable catheter", Gibson, Charles A.

39. U.S. Pat. No. 7,232,422, Jun. 19, 2007, "Steerable catheter", Gibson, Charles A., et al.

40. U.S. Patent Application Publication No. 20060247522, Nov. 2, 2006, "Magnetic navigation systems with dynamic mechanically manipulatable catheters", McGee, David L.

41. U.S. Pat. No. 6,783,510, Aug. 31, 2004, "Steerable catheter", Gibson, Charles A., et al.

42. U.S. Patent Application Publication No. 20080015625, Jan. 17, 2008, "Shapeable for steerable guide sheaths and methods for making and using them", Ventura, Christine P., et al.

FIGS. 5(A)-5(D) schematically illustrate a number of embodiments of the epicardial pacing catheter 10 of the epicardial pacing system near the distal portion.

Figure 5B:
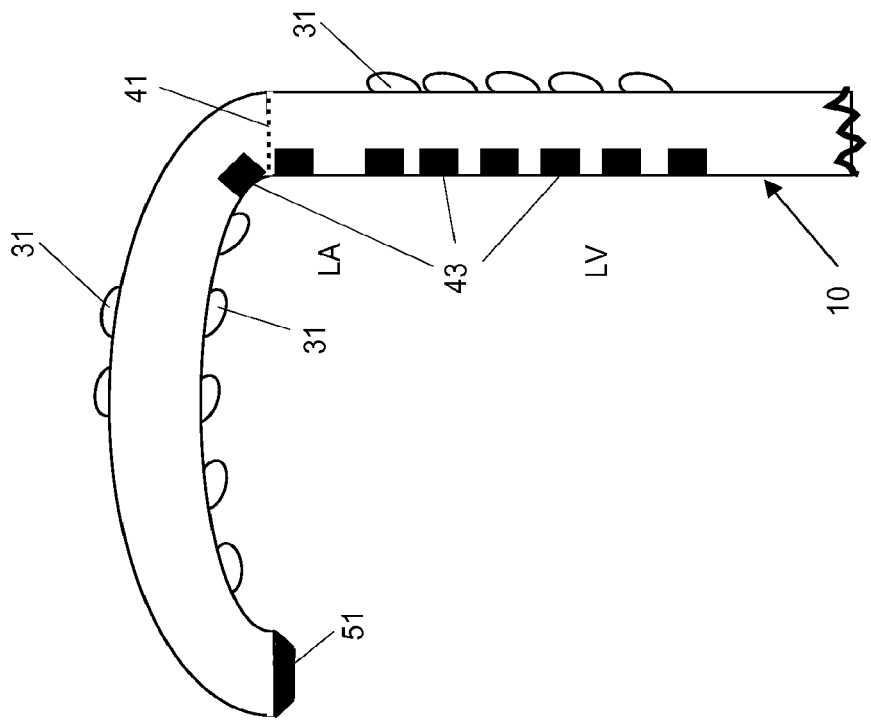
FIGS. 5(A)-5(D) schematically illustrate a number of exemplary embodiments of the epicardial pacing catheter 10 near the distal portion.
Figure 5A:
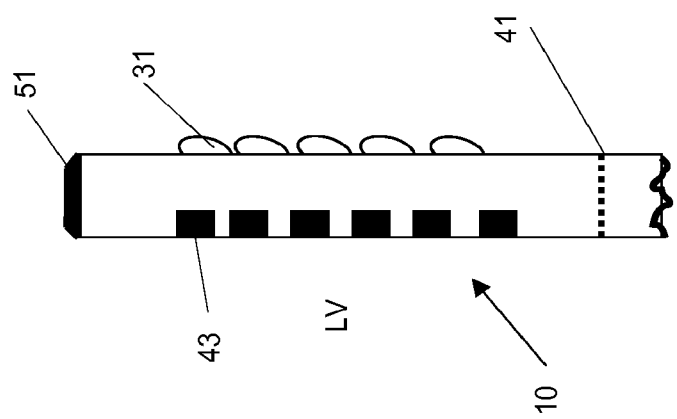

FIG. 5(A) schematically illustrates an exemplary embodiment wherein the epicardial pacing catheter 10 may be used to pace the left ventricle (LV) of a patient's heart. A number of electrodes 43 are adapted to transmit electrical energy to the left ventricle, and are shown facing the left ventricle. The number of electrodes 43 may vary depending on the number of locations required or desired to be paced. The electrodes 43 may be insulated on at least one side away from the heart, as to prevent electrical energy from being transmitted to proximate anatomical structures. The insulation may be about 2 mm thick, and may extend longitudinally through the epicardial pacing catheter 10. It should be appreciated that the thickness may be wider or narrower as desired or required according to medical procedures, device/system operations and anatomical considerations. Further, the insulation may comprise Teflon, silicone, polyurethane, and/or any combination thereof or any other non-conductive material known in the art.

Outward facing bumper tabs 31 are deployable, and are used to stabilize the epicardial pacing catheter 10 by pushing against the pericardium. As shown, the outward facing bumper tabs 31 are in the non-deployed state as to allow the epicardial pacing catheter 10 to move within the pericardium. Although not shown, the epicardial pacing catheter may further comprise inward facing friction tabs 32 or other stabilization means.

The epicardial pacing catheter 10 further comprises a distal tip 51 in communication with the epicardial pacing catheter 10. The distal tip 51 extends from the body of the catheter 10 and may further insulate the electrodes 43 from proximate anatomical structures and/or be used to push through harder anatomical structures and adhesions as desired or required.

FIG. 5(B) schematically illustrates an exemplary embodiment wherein the epicardial pacing catheter 10 may be used to pace the left ventricle (LV) and left atrium (LA) of a patient's heart. Additional electrodes 43 near the distal point of curvature 41 are shown. These electrodes 43 may be in communication with the outside wall of the left atrium in order to pace said structure. Additional outward facing bumper tabs 31 are present to press against the pericardium in more distal locations. Inward facing friction tabs 32 are now shown. The inward facing friction tabs 32 may be deployed to catch, drag, stick to, or pull on adjacent anatomical structures to keep the epicardial pacing catheter 10 from moving. FIG. 5(B) shows an example embodiment wherein both the inward facing friction tabs 32 and outward facing bumper tabs 33 are in the non-deployed state to allow movement of the catheter 10.

Figure 5D:
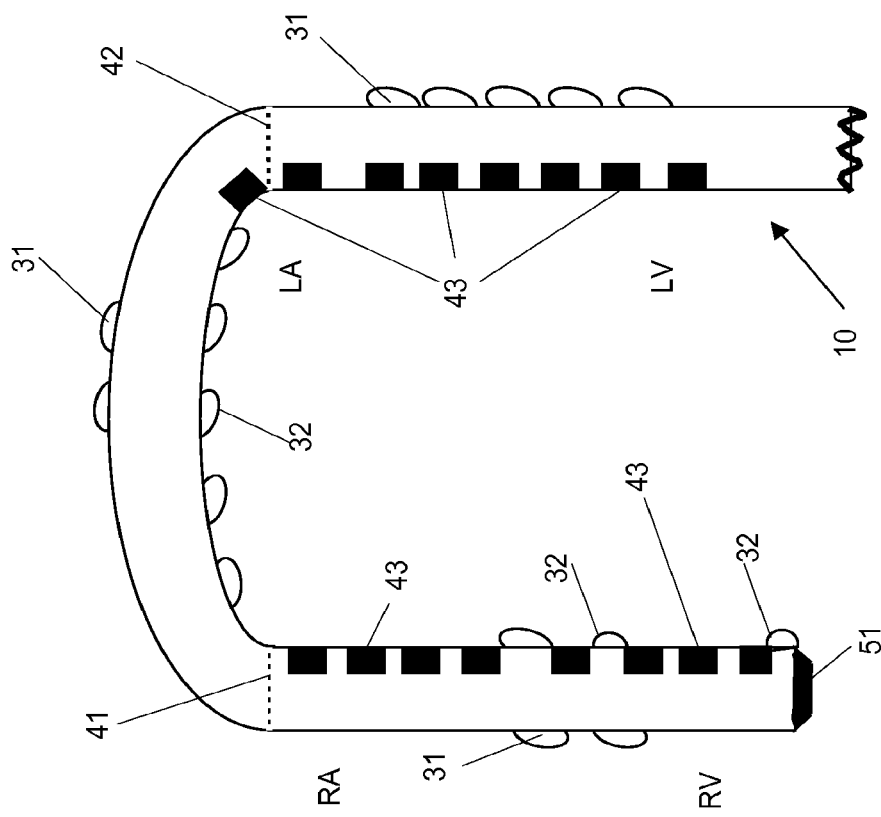
Figure 5C:
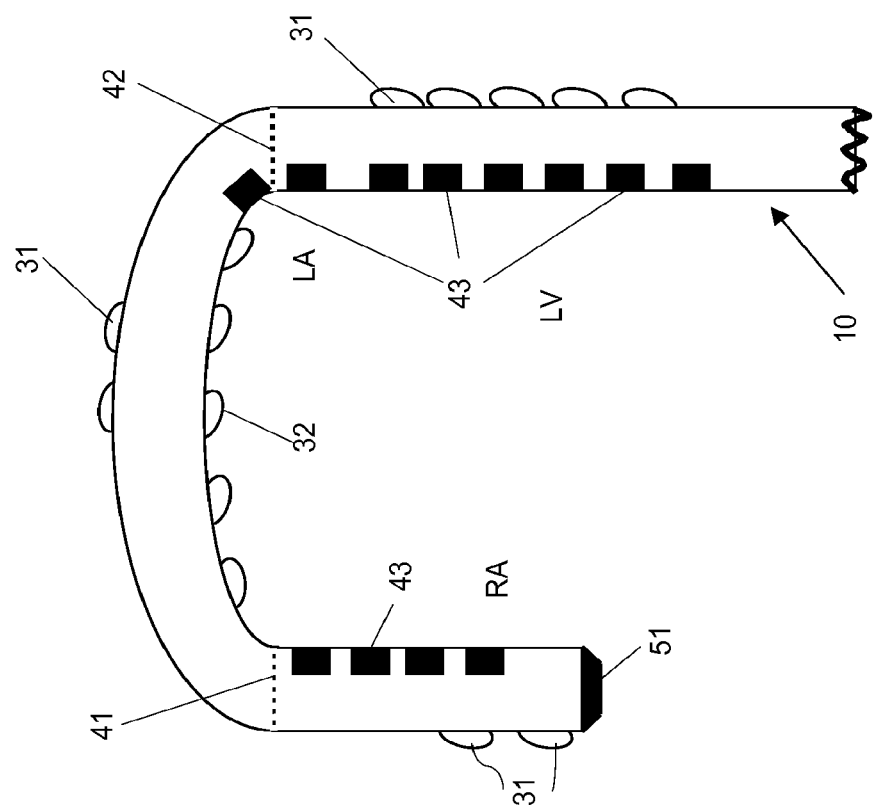

FIG. 5(C) schematically illustrates an exemplary embodiment wherein the epicardial pacing catheter 10 may be used to pace the left ventricle (LV), left atrium (LA), and right atrium (RA). Additional electrodes 43 are located near the distal point of curvature 41. These electrodes 43 may be in communication with the outside wall of the right atrium in order to pace said structure. Further, additional outward facing bumper tabs 31 are present to press against the pericardium in more distal locations.

FIG. 5(D) shows an example embodiment wherein the epicardial pacing catheter 10 may be used to pace multiple points on the left ventricle (LV), left atrium (LA), right atrium (RA), and right ventricle (RV). Additional electrodes 43 are shown in a more distal location in order to transmit electrical energy to the right ventricle. Further, additional inward facing bumper tabs 32 are present to catch, drag, stick to, or pull on adjacent anatomical structures to keep the epicardial pacing catheter 10 from moving.

It should be appreciated that in FIGS. 5(A)-5(D) both the number of inward facing friction tabs 32 and outward facing bumper tabs 31 may vary as desired or required to stabilize the epicardial pacing catheter 10. Moreover, inward facing friction tabs 32 may be located proximal or distal to any outward facing bumper tab 31. Further, outward facing bumper tabs 31 may be located proximal or distal to any inward facing friction tab 32. Further, outward facing bumper tabs 31 and inward facing friction tabs 32 may be positioned at the same location on the epicardial pacing catheter 10 as desired or required.

It should be appreciated that in FIGS. 5(A)-5(D) any number of electrodes 43 may be present as desired or required to pace a number of locations on the heart of a patient. Moreover, each electrode 43 could be turned on separately in a unipolar or bipolar fashion, allowing for pacing of different chambers and different parts of the same chamber at different times. This has an important advantage: if a region of tissue ever dies in heart attack, pacing can be accomplished from a different location.

It should be appreciated that the inward facing friction tabs and outward facing bumper tabs may be alternated with one another, be staggered with one another, or grouped in numbers among each other as desired or required according to medical procedures, device/system operations and anatomical considerations.

FIGS. 6(A)-6(F) schematically illustrate cross sectional views of an exemplary embodiment of the epicardial pacing catheter 10 of the epicardial pacing system from the most distal end to a more proximal point.

Figure 6C:
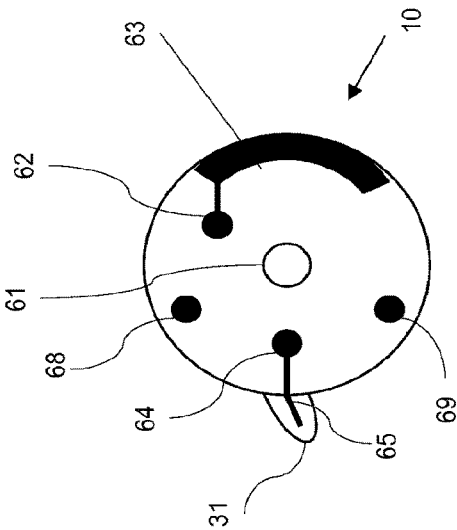
FIGS. 6(A)-6(F) schematically illustrate cross sectional views of an exemplary embodiment of the technology from the most distal end to a more proximal point.
Figure 6B:
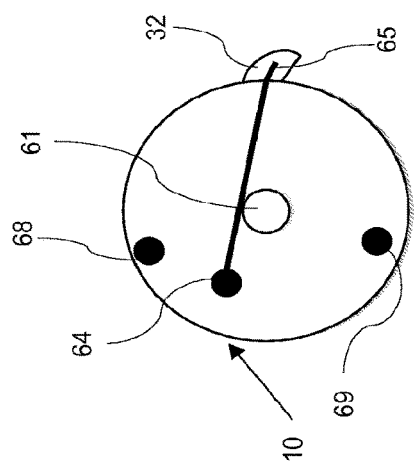
Figure 6A:
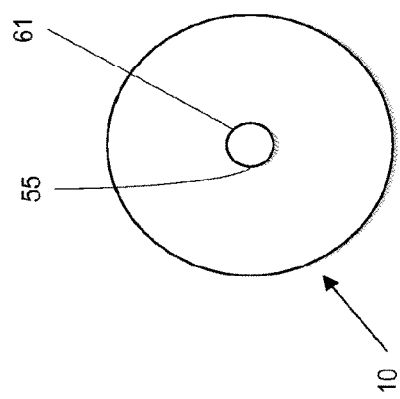

FIG. 6(A) schematically illustrates a cross sectional view of an exemplary embodiment of the most distal portion of the epicardial pacing catheter 10 of the epicardial pacing system. The epicardial pacing catheter 10 further comprises a fluid lumen 61. The fluid lumen occupies internal cross-sectional area of the epicardial pacing catheter 10. The fluid lumen 61 may extend from an aperture (not shown) in the proximal end of the catheter 10 to a distal fluid aperture 55. Both the distal fluid aperture 55 and a proximal fluid aperture (not shown) are adapted for the emitting and extracting of a fluid, drug, or agent. The fluid, drug, or agent may be used, but is not necessarily used, to cool the electrodes 43, regulate heart activity, or distend proximal anatomical structures. The proximal fluid aperture (not shown) is connected to an external fluid, drug, or agent source (not shown). The emitting and extracting of a fluid, drug, or agent may be controlled by an external control handle 150 (as shown, for example, in FIG. 15) in communication with the proximal end and fluid, drug, or agent source. It should be appreciated that the fluid, drug, or agent to flow through the epicardial pacing catheter 10 may be at least one of the following: agent, substance, material, saline solutions, thrombolytic agents, clot lysis agents, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic agent and/or diagnostic agent or any combination thereof.

FIG. 6(B) schematically illustrates a more proximal cross section of an example embodiment of the epicardial pacing catheter 10 of the epicardial pacing system located proximal to the distal point of curvature 41. Both the first distal steering pull-wire 68 and second distal steering pull-wire 69 occupy internal cross-sectional area of the epicardial pacing catheter 10 and extend longitudinally to the most proximal portion of said catheter 10. The first distal steering pull-wire 68 and second distal steering pull-wire 69 may be controllably connected to a control means (as shown, for example, in FIG. 15) in communication with the proximal portion of the epicardial pacing catheter 10.

The epicardial pacing catheter 10 may further comprise a stabilization means. The stabilization means may be deployable and may comprise an inward facing friction tab 32, an outward facing bumper tab 31, a non-deployable protrusion, a screw, a hook, or other means known in the art.

In an example embodiment, a tab deployment rod 64 extends longitudinally from the most proximal portion of the epicardial pacing lead 10 to the most distal inward facing friction tab 32 or outward facing bumper tab 31. The tab deployment rod 64 may be a longitudinal structure, such as, but not limited to, a push-rod, pull-rod, wire, string, or rope. The tab deployment rod 64 made be made of a non-conductive material having high tensile strength as is known in the art. The tab deployment rod 64 may further be controllably connected to a control means (as shown, for example, in FIG. 15) in communication with the epicardial pacing catheter 10, said control means used to control the deployment of the stabilization means. Further, the tab deployment rod 64 is in communication with a number of tab deployment arms 65, wherein each tab deployment arm 65 can be actuated to deploy the inward facing friction tab 32 or outward facing bumper tab 31.

FIG. 6(C) schematically illustrates a more proximal cross section of an exemplary embodiment of the epicardial pacing catheter 10 of the epicardial pacing system. The anode wire 62 extends longitudinally from the most proximal portion of the epicardial pacing catheter 10 to the most distal anode 63. The anode wire 62 may be in communication with one or more anodes 63 located throughout the epicardial pacing catheter 10. Further, the anode wire 62 is adapted for transmitting and receiving electrical energy. The anode wire 62 may be controllably connected to a control means (as shown, for example, in FIG. 15) in communication with the proximal portion of the epicardial pacing catheter 10.

An outward facing bumper tab 31 is shown in communication with the epicardial pacing catheter 10. The outward facing bumper tab 31 may be deployed by a tab deployment arm 65 in communication with the tab deployment rod 64.

Figure 6F:
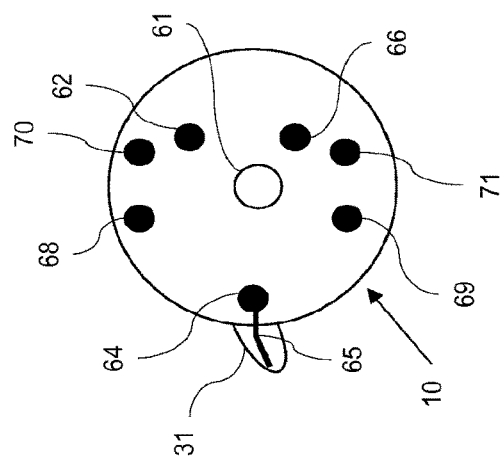
Figure 6E:
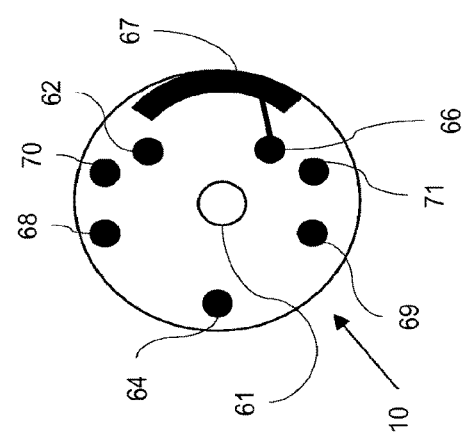
Figure 6D:
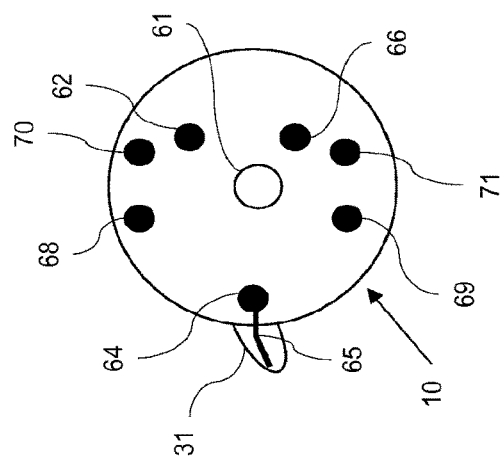

FIG. 6(D) schematically illustrates a more proximal cross section of an exemplary embodiment of the epicardial pacing catheter 10 of the epicardial pacing system located proximal to the proximal point of curvature 42. The epicardial pacing catheter 10 further comprises a second steering means. The second steering means comprises a first proximal steering pull-wire 70 and a second proximal steering pull-wire 71. Both the first proximal steering pull-wire 70 and second proximal steering pull-wire 71 occupy internal cross-sectional area of the epicardial pacing catheter 10 and extend longitudinally to the most proximal portion of said catheter 10. The first proximal steering pull-wire 70 and second proximal steering pull-wire 71 may be controllably connected to a control means (as shown, for example, in FIG. 15) in communication the proximal portion of the epicardial pacing catheter 10.

FIG. 6(E) schematically illustrates a more proximal cross section of an example embodiment of the epicardial pacing catheter 10 of the epicardial pacing system. A cathode wire 66 extends longitudinally from the most proximal portion of the epicardial pacing catheter 10 to the most distal cathode 67. The cathode wire 66 may be in communication with one or more cathodes 67 located throughout the epicardial pacing catheter 10. Further, the cathode wire 66 is adapted for transmitting and receiving electrical energy. The cathode wire 66 may be controllably connected to a control means (as shown, for example, in FIG. 15) in communication with the proximal portion of the epicardial pacing catheter 10.

FIG. 6(F) schematically illustrates a more proximal cross section of an example embodiment of the epicardial pacing catheter 10 of the epicardial pacing system. An outward facing bumper tab 31 is shown in communication with the epicardial pacing catheter 10. The outward facing bumper tab 31 may be deployed by a tab deployment arm 65 in communication with a tab deployment rod 64. It should be appreciated that the number of port holes, lumens, wires or rods may vary as may be desired or required according to medical procedures, device/system operations and anatomical considerations.

FIGS. 7(A) and 7(B) schematically illustrate a cross sectional view of an exemplary embodiment of the proximal end 73 of the epicardial pacing catheter 10 of the epicardial pacing system and the most distal end 74 of the control means 150 respectively. In FIG. 7(A), twelve electrode wires, including six anode wires 62 and six cathode wires 66, occupy internal cross-sectional area of the epicardial pacing catheter 10. Each anode wire 62 and cathode wire 66 extends longitudinally through the epicardial pacing catheter 10 towards the distal portion. The cathode wire 66 may be in communication with one or more cathodes 67 located throughout the epicardial pacing catheter 10. The anode wire 62 may be in communication with one or more anodes 63 located throughout the epicardial pacing catheter 10.

It should be appreciated that any number of electrodes 43, otherwise known as anodes 63 and cathodes 67, may be present as desired or required to pace a number of locations on the heart of a patient. A single anode wire 62 may be used to provide electrical energy to a multitude of anodes 63, or each anode wire 62 can provide electrical energy to a single anode 63. A single cathode wire 66 may be used to provide electrical energy to a multitude of cathodes 67, or each cathode wire 66 can provide electrical energy to a single cathode 67. Moreover, electrical energy can be transmitted to each electrode 43 separately in a unipolar or bipolar fashion, allowing for pacing of different chambers and different parts of the same chamber at different times.

Further, a first proximal steering pull-wire 70, first distal steering pull-wire 68, second proximal steering pull-wire 71, and second distal steering pull-wire 69 occupy internal cross-sectional area of the epicardial pacing catheter 10. Each first proximal steering pull-wire 70, first distal steering pull-wire 68, second proximal steering pull-wire 71, and second distal steering pull-wire 69 extends longitudinally through the epicardial pacing catheter 10 towards the distal portion. Each first proximal steering pull-wire 70, first distal steering pull-wire 68, second proximal steering pull-wire 71, and second distal steering pull-wire 69 may comprise guidewires, tensioning lines, pull strings, digitating distal tips, magnetic guidance means, wires, rods, chains, bands, chords, ropes, string tubes, filaments, threads, fibers, strands, other extended elements, or any other method known in the art.

Further, a first tab deployment rod 64 and second tab deployment rod 72 occupy internal cross-sectional area of the epicardial pacing catheter 10. Each first tab deployment rod 64 and second tab deployment rod 72 extends longitudinally from the most proximal portion 73 of the epicardial pacing lead 10 to the most distal inward facing friction tab 32 or outward facing bumper tab 31. The first tab deployment rod 64 and second tab deployment rod 72 may comprise a longitudinal structure, such as, but not limited to, a push-rod, pull-rod, wire, string, magnetic guidance means, chains, bands, chords, or rope. The first tab deployment rod 64 and second tab deployment rod 72 may comprise a non-conductive material having high tensile strength as is known in the art. The first tab deployment rod 64 and second tab deployment rod 72 may further be controllably connected to the distal end 74 of a control means 150 in communication with the proximal end 73 of the epicardial pacing catheter 10, said control means used to control the deployment of the tabs.

It should be noted that, while a first tab deployment rod 64 and second tab deployment rod 72 are shown, any number of tab deployment rods may be present as desired or required, up to an including the sum of inward facing friction tabs 32 and outward facing bumper tabs 31 (See FIGS. 6(A)-(E)).

Although not shown, in an example embodiment, a biocompatible cover may be in communication with the most proximal end 73 of the epicardial pacing catheter 10. The biocompatible cover may prevent fibrosis from occurring around the exposed structures of the epicardial pacing catheter 10.

Although not shown, in an example embodiment, the proximal end 73 of the epicardial pacing catheter 10 may be located just under the skin of a patient. The proximal end 73 can be reached by a non-surgical, minimally-invasive incision of the skin, carried out by a clinician or cardiologist.

Although not shown, in an example embodiment, all structures beginning at the proximal end 73 may protrude from said proximal end 73 of the epicardial pacing catheter 10. In this way, the proximal end 73 could act as a male connector in a male-female connection. It should be appreciated that the corresponding male-female connection may be reversed as well.

FIG. 7(B) shows a cross sectional view of an example embodiment of the most distal portion 74 of a control handle 150. In this particular embodiment, the control handle 150 can be controllably connected to the most proximal portion 73 of the epicardial pacing catheter 10. Wire grippers 75 around each of the internal structures facilitate a secure connection between structures integral the control handle 150 and structures integral the epicardial pacing catheter 10.

Although not shown, in an example embodiment, all structures within the control handle 150 may end before the distal end 74. In this way, the distal end 74 can act as a female connector in a male-female connection.

It should be appreciated that the number of lumens, wires, rods or elements discussed with regards to FIG. 7 may vary as may be desired or required according to medical procedures, device/system operations and anatomical considerations.

FIGS. 8(A)-(C) schematically illustrate cross-sectional views of an example embodiment wherein the epicardial pacing catheter 10 further comprises a stabilization means for stabilizing the epicardial pacing catheter 10. The stabilization means may comprise at least one deployable member. The stabilization means allows the rotational orientation of the distal portion of the epicardial pacing catheter 10 to remain fixed in place relative to the surface of the heart. If the distal portion of the epicardial pacing catheter 10 were allowed to rotate so that the electrodes 43 faced away from the heart, pacing could not be achieved and adjacent anatomical structures would receive harmful electronic energy.

FIGS. 8(A)-(C) illustrate an exemplary embodiment wherein the stabilization means is an inward facing friction tab 32. The inward facing friction tab 32 comprises a catheter-side surface 82 and an anatomical-side surface 83. The anatomical-side surface 83 comprises a lubricious surface that may be navigated through anatomical structures without sticking or catching. The catheter-side surface 82 comprises a rough surface having a larger coefficient of friction than the anatomical-side surface. The catheter-side surface may further comprise a textured surface to increase friction. Both the catheter-side surface 82 and anatomical-side surface 83 comprise a non-conductive material, such as, but not limited to polyurethane, Teflon, silicone, a radio-opaque material, or similarly lubricious material, or other materials known in the art.

FIG. 8(A) illustrates an exemplary embodiment wherein the stabilization means further comprises a stabilizer actuator, wherein said stabilizer actuator deploys the inward facing friction tab 32. Though the stabilizer actuator is illustrated as a tab deployment rod 64 in communication with a tab joint 84, tab hinge 81, and tab deployment arm 65, the stabilizer actuator may comprise any longitudinal member in communication with at least one of the following:

gear, hinge, joint, rack and pinion, pulley, linear actuator, or linear-rotational actuator, or any combination thereof. Further, the longitudinal member may be, for example, a push-rod, pull-wire, wire, string, rope, pole, thread, filament, cord, strand or other means known in the art. The stabilizer actuator may further comprise a micro electrical mechanical system (MEMS).

In an embodiment, a tab deployment rod 64 extends longitudinally from the most proximal portion of the epicardial pacing lead 10 to the most distal inward facing friction tab 32. The tab deployment rod 64 may be a longitudinal structure, such as, but not limited to, a push-rod, pull-rod, wire, string, pole, thread, filament, cord, strand or rope. The tab deployment rod 64 made be made of a non-conductive material having high tensile strength as is known in the art. The tab deployment rod may further be controllably connected to a control means or control handle (as shown, for example, in FIG. 15) in communication with the epicardial pacing catheter 10 of the epicardial pacing system 5, and the control means may be used to control the deployment of the tabs.

The tab deployment rod 64 is in communication with a tab joint 84, the tab joint 84 in connection with a tab deployment arm 65 having its endpoint within the inward facing friction tab 32. The tab deployment arm is in further communication with a tab hinge 81.

When the inward facing friction tab 32 is in the non-deployed state, the epicardial pacing catheter 10 may be moved, navigated, or slid within the middle mediastinum. In this way, the epicardial pacing catheter 10 can be inserted, placed, navigated or removed from the pericardial sack.

FIG. 8(B) illustrates an embodiment wherein the stabilization means is an inward facing friction tab 32 in the partially-deployed state. When the tab deployment rod 64 is pushed toward the distal end of the epicardial pacing catheter 10, the tab deployment arm 65 is pulled or tensioned. This causes the inward facing friction tab 32 to separate from the catheter body, exposing the rough catheter-side 82 to proximate anatomical structures.

FIG. 8(C) illustrates an embodiment wherein the stabilization means is an inward facing friction tab 32 in the fully-deployed state.

Although not shown, the outward facing bumper tabs 31 may be deployed using the same means and methods as described above.

Although not shown, the stabilization means may comprise one or more protrusions for engaging proximal anatomical structures such as the pericardium and/or the epicardium. The protrusions may be non-deployable. Further, the protrusions may comprise a non-conductive material, such as, but not limited to, silicone, polyurethane, Teflon, a radio-opaque material, or other materials known in the art.

It should be appreciated that the hinge devices and joint devices may be a number of elements such as, but not limited thereto, a fulcrum, swivel, gear, elbow, pivot, thrust or the like.

It should be appreciated that the tab devices may be a number of elements such as, but not limited thereto, finger, stud, post, tongue, spring, projection, pin, pedestal, extension, offset, knob, protuberance or the like.

Figure 9:
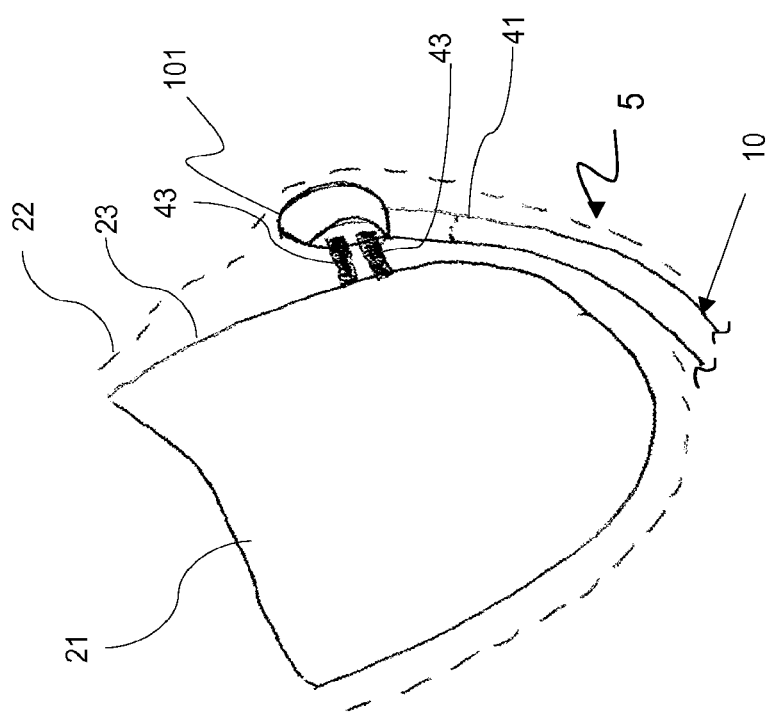
FIG. 9 schematically illustrates an example embodiment of the epicardial pacing catheter further comprising deployable electrodes fixed or adjacent to the heart.

FIG. 9 schematically illustrates an example embodiment of the epicardial pacing catheter 10 of the epicardial pacing system in relation to the heart 21 and further comprising at least one deployable member. The epicardial pacing catheter 10 has been steered around its distal point of curvature 41, and is positioned in the pericardial space, cavity or sack 24, or the area between the pericardium 22 and epicardium 23.

In an embodiment, the deployable member comprises at least one electrode 43, and each electrode 43 is facing the heart 21. The electrodes 43 may be deployed from the epicardial pacing catheter 10 and are fixed to the epicardium 23 when in the fully-deployed state. The epicardial pacing catheter 10 may further comprises an insulating hood 101 in communication with the epicardial pacing catheter 10.

Figure 10B:
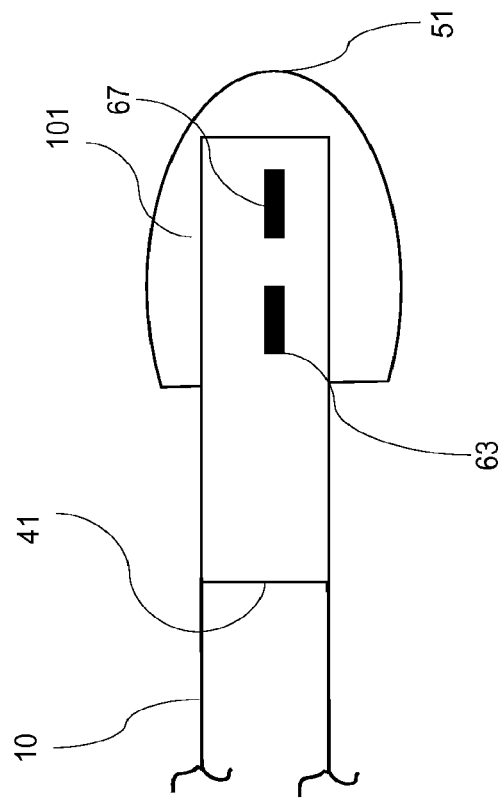
FIG. 10(B) schematically illustrates a bottom view of an exemplary embodiment of the epicardial pacing catheter.
Figure 10A:
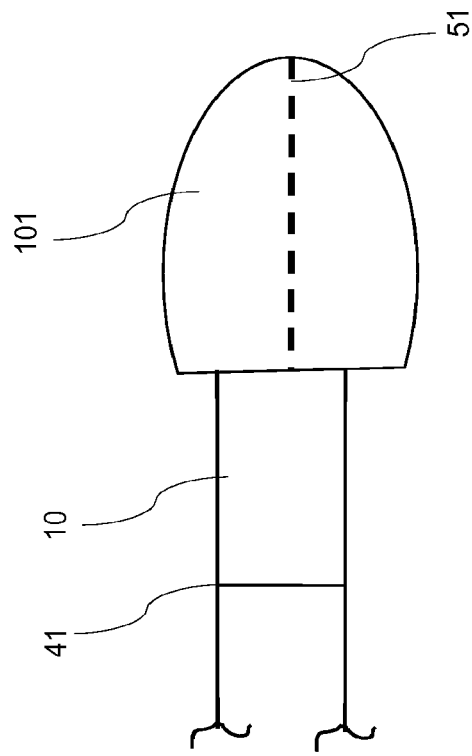
FIG. 10(A) schematically illustrates a top view of an exemplary embodiment of the epicardial pacing catheter.

FIG. 10(A) schematically illustrates a top view of an example embodiment of the epicardial pacing catheter 10 of the epicardial pacing system. The epicardial pacing catheter further comprises a insulating hood 101 extending from beyond the distal point of curvature 41 to a distal tip 51. The hood may serve as a cushioning and/or alignment means for the distal tip 51 relative to adjacent anatomical structures. It should be appreciated that some portion of the distal tip shall have insulation to protect from adjacent anatomical structures. The shape of the distal tip and hood may vary according to medical procedures, device/system operations and anatomical considerations.

FIG. 10(B) schematically illustrates a bottom view of an exemplary embodiment of the epicardial pacing catheter 10 of the epicardial pacing system. An anode 63 and cathode 67 are shown in communication with the epicardial pacing catheter 10. In an embodiment, the contact zones containing the anode 63 and cathode 67 electrodes are about 2 mm in length and about 1 mm in width, and are located centrally within the underside surface of the insulating hood 101. It should be appreciated that the width of the electrodes may be longer or shorter as may be desired or required according to medical procedures, device/system operations and anatomical considerations. The insulating hood extends from a distal location beyond the distal point of curvature 41 to a distal tip 51.

FIG. 10(C) schematically illustrates an axial view of an exemplary embodiment of the epicardial pacing catheter 10 of the epicardial pacing system looking at the distal tip 51 of the insulating hood 101. A single electrode 43 can be seen on the underside of the epicardial pacing catheter 10.

FIG. 10(D) schematically illustrates a side view of an exemplary embodiment of the epicardial pacing catheter 10 comprising an insulating hood 101, distal tip 51, and two electrodes 43. The insulating hood 101 extends over the side of the epicardial pacing catheter 10.

It should be appreciated that in FIGS. 10(A)-(D) any number of electrodes 43 may be present as desired or required to pace any number of locations on the heart of a patient. Moreover, each electrode 43 could be powered separately in a unipolar or bipolar fashion, allowing for pacing of different parts of the same chamber at different times.

FIG. 11(A)-11(E) schematically illustrate cross sectional views of an exemplary embodiment of the epicardial pacing catheter 10 of the epicardial pacing system from a point located proximal to the most distal anode 62 or cathode 67 and distal to the distal point of curvature 41 to a point located at the most proximal point 73 of the epicardial pacing catheter 10. FIG. 11(F) schematically illustrates a cross sectional view of an exemplary embodiment of the external control handle 150 at the most distal point 74.

Figures 11A, 11B, 11C, 11D, 11E, 11F:
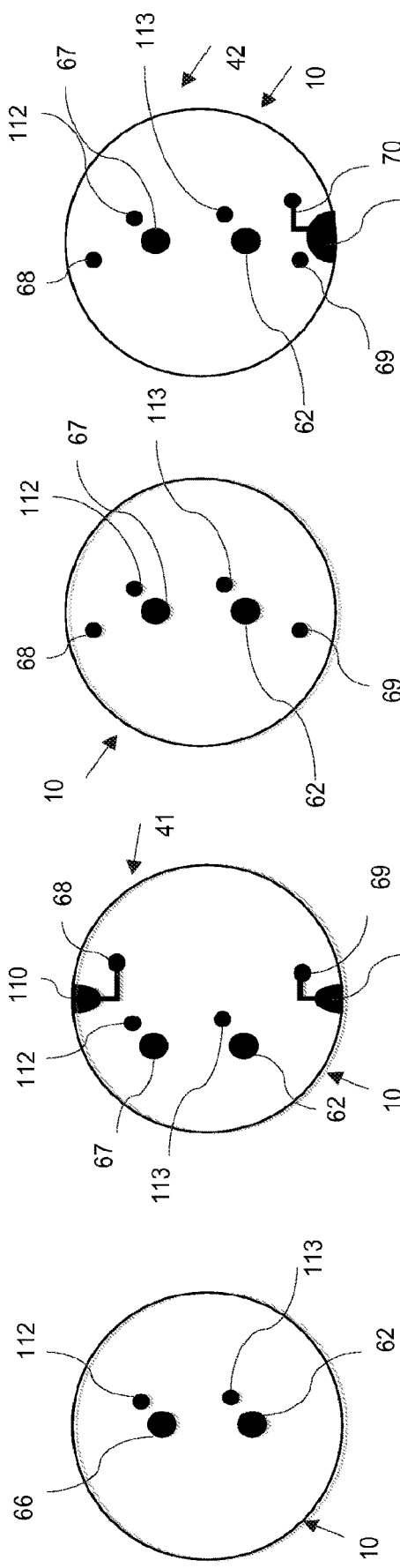
FIG. 11(A)-11(E) schematically illustrate cross sectional views of an exemplary embodiment of the epicardial pacing catheter from a point located proximal to the at least one electrode and distal to the distal point of curvature to a point located at the most proximal point of the epicardial pacing catheter.
FIG. 11(F) schematically illustrates a cross sectional view of an exemplary embodiment of the control handle at the most distal point.

FIG. 11(A) schematically illustrates a cross section of an example embodiment of the epicardial pacing catheter 10 located more distal than the distal point of curvature 41 and proximal to the most distal anode 62 or cathode 67. An anode wire 62, cathode wire 66, electrode pull-wire 112, and second-electrode pull-wire 113 occupy internal cross-sectional area of the epicardial pacing catheter 10 and extend longitudinally to the most proximal portion 73 of said catheter 10. The anode wire 62, cathode wire 66, electrode pull-wire 112, and second-electrode pull-wire 113 may comprise longitudinal structures, such as, but not limited to, push-rods, pull-rods, wires, strings, or ropes. Further, the anode wire 62, cathode wire 66, electrode pull-wire 112, and second-electrode pull-wire 113 may be controllably connected to a control handle 150 in electrical communication with the most proximal point 73 of the epicardial pacing catheter 10.

The anode wire 62 and electrode pull-wire 112 extend longitudinally from the most proximal portion 73 of the epicardial pacing catheter 10 to the most distal anode 63. The cathode wire 66 and second electrode pull-wire 113 extend longitudinally from the most proximal portion 73 of the epicardial pacing catheter 10 to the most distal cathode 67.

FIG. 11(B) schematically illustrates a more proximal cross section of an example embodiment of the epicardial pacing catheter 10 located at the distal point of curvature 41. The epicardial pacing catheter 10 further comprises a first distal steering pull-wire 68 and a second distal steering pull-wire 69 fixed to distal steering anchors 110 in communication with the epicardial pacing catheter 10. The distal steering anchors 110 comprise a material with requisite strength to hold the first distal steering pull-wire 68 and second distal steering pull-wire 69 in place. The first distal steering pull-wire 68 and second distal steering pull-wire 69 occupy internal cross-sectional area of the epicardial pacing catheter 10 and extend longitudinally to the most proximal point 73 of said catheter 10. The first proximal steering pull-wire 68 and second proximal steering pull-wire 69 may be controllably connected to a control handle 150 in communication with the most proximal point 73 of the epicardial pacing catheter 10.

FIG. 11(C) schematically illustrates a more proximal cross section of an example embodiment of the epicardial pacing catheter 10 located between the distal point of curvature 41 and proximal point of curvature 42.

FIG. 11(D) schematically illustrates a more proximal cross section of an example embodiment of the epicardial pacing catheter 10 located at the proximal point of curvature 42. The epicardial pacing catheter 10 further comprises a proximal steering pull-wire 70 fixed to a proximal steering anchor 111 in communication with the epicardial pacing catheter 10. The proximal steering anchor 111 comprises a material with requisite strength to hold the proximal steering pull-wire 70. The proximal steering pull-wire 70 occupies internal cross-sectional area of the epicardial pacing catheter 10 and extends longitudinally to the most proximal point 73 of said catheter 10. The proximal steering pull-wire 70 can be controllably connected to a control handle 150 or control means in communication with the most proximal point 73 of the epicardial pacing catheter 10.

FIG. 11(E) schematically illustrates a more proximal cross section of an example embodiment of the epicardial pacing catheter 10 located at the most proximal point 73.

It should be noted that, while a single anode wire 62, electrode pull-wire 112, cathode wire 66, and second electrode pull-wire 113 are shown, any number of anode wires 62, electrode pull-wires 112, cathode wires 66, and second electrode pull-wires 113 may be present as desired or required, up to and including, for example, the total number of electrodes 43 (or the sum of the anodes 63 and cathodes 67).

Although not shown, in an example embodiment, a biocompatible cover may be in communication with the most proximal end 73 of the epicardial pacing catheter 10. The biocompatible cover can prevent fibrosis from occurring around the exposed wires of the epicardial pacing catheter 10.

Although not shown, in an example embodiment, the proximal end 73 of the epicardial pacing catheter 10 is located just under the skin of a patient (or location(s) as desired or required). The proximal end 73 can be reached by a non-surgical, minimally-invasive incision of the skin, carried out by a clinician or cardiologist.

Although not shown, in an example embodiment, all structures beginning at the proximal end 73 may protrude from said proximal end 73 of the epicardial pacing catheter 10. In this way, the proximal end 73 could act as a male connector in a male-female connection. The male-female arrangement may be reversed if desired or required.

FIG. 11(F) schematically illustrates a cross sectional view of an example embodiment of the most distal portion 74 of a control handle 150. In this particular embodiment, the control handle 150 can be controllably connected to the most proximal portion 73 of the epicardial pacing catheter 10. Wire grippers 75 (or other retention means or devices) around each of the internal structures facilitate a secure connection between structures integral the control handle 150 and structures integral the epicardial pacing catheter 10.

Although not shown, in an example embodiment, all structures within the control handle or control means may end before the distal end 74. In this way, the distal end 74 can act as a female connector in a male-female connection (or female-male connection).

FIG. 12(A) schematically illustrates a cross section of an exemplary embodiment of the epicardial pacing catheter 10 of the epicardial pacing system comprising a deployable stabilization means in an un-deployed state. The deployable stabilization means comprises an anode 63 and cathode 67 in communication with a hook 124. The hook 124, anode 63, and cathode 67 comprise conductive materials, such as, but not limited to, copper, platinum, gold, silver or iridium, and/or alloys thereof.

The stabilization means further comprises a stabilizer actuator, wherein said stabilizer actuator deploys the anode 63 and cathode 67 in communication with the hooks 124. Though the stabilizer actuator is illustrated as an electrode pull-wire 112 in communication with a joint 121, and hinge 122, the stabilizer actuator may comprise any longitudinal member in communication with at least one of the following: gear, hinge, joint, rack and pinion, pulley, linear actuator, or linear-rotational actuator, or any combination thereof. Further, the longitudinal member may be, for example, a push-rod, pull-wire, wire, string, rope, pole, thread, filament, cord, strand or other means known in the art. The stabilizer actuator may further comprise a micro electrical mechanical system (MEMS).

It should be appreciated that the hook devices may be a number of elements such as, but not limited thereto, pin, claw, latch, finger, stud, spring, post, tongue, projection, pin, pedestal, extension, offset, knob, protuberance or the like.

In an embodiment, an electrode pull-wire 112 extends longitudinally from the most proximal portion of the epicardial pacing lead 10 to the most distal electrode 43, which may comprise an anode 63 or cathode 67. The electrode pull-wire 112 is in communication with a joint 121, the joint 121 in further communication with a hinge 122.

In an embodiment, the electrode pull-wire 112 may comprise a conductive material having high tensile strength as is known in the art. The electrode-pull wire 112 may further be controllably connected to a control means (for example, as shown in FIG. 15) in communication with the epicardial pacing catheter 10 and epicardial pacing system. The control means may be used to control the deployment of the anode 63 and cathode 67 in communication with hooks 124, and any of the devices, systems, subsystems, elements, and devices discussed throughout this disclosure.

In an embodiment, the epicardial pacing catheter 10 further comprises an insulating distal tip 51 in communication with the epicardial pacing catheter. The epicardial pacing catheter 10 further comprises a number of bumpers 120 in communication with the bottom of the epicardial pacing catheter 10. In an approach, the bumpers enable the epicardial pacing catheter 10 to sit on the surface of the heart in a non-deployed state without allowing the anode 63 or cathode 67 to be in communication with the epicardium.

When the deployable anode 63 and cathode 67 are in the non-deployed state, the epicardial pacing catheter 10 may be moved or navigated within the middle mediastinum. In this way, the epicardial pacing catheter 10 can be inserted, placed, navigated or removed from the pericardial sack.

FIG. 12(B) schematically illustrates a cross section of an exemplary embodiment of the epicardial pacing catheter 10 comprising a deployable anode 63 and cathode 67 in a fully-deployed state. When the electrode pull-wire 112 is pushed toward the distal end of the epicardial pacing catheter 10, the anode 63 and cathode 67 are splayed outward to a 90 degree angle, or an angel(s) as desired or required. This causes the anode 63 and cathode 67 to separate from the catheter body, allowing the hooks 124 to engage proximate anatomical structures, such as the epicardial wall. When the deployable anode 63 and cathode 67 are in the fully-deployed state, the rotational orientation of the distal portion of the epicardial pacing catheter 10 remains fixed in place relative to the surface of the heart. If the distal portion of the epicardial pacing catheter 10 were allowed to rotate so that the electrodes 43 faced away from the heart, pacing could not be achieved and adjacent anatomical structures would receive harmful electronic energy.

It should be appreciated that in FIGS. 12(A) and (B) any number of deployable electrodes 43 may be present as desired or required to pace any number of locations on the heart of a patient.

It should be appreciated that when the electrode pull-wire 112 is pulled toward the proximal end of the epicardial pacing catheter 10, the anode 63 and cathode 67 are drawn back into place within the catheter 10.

Figure 13A:
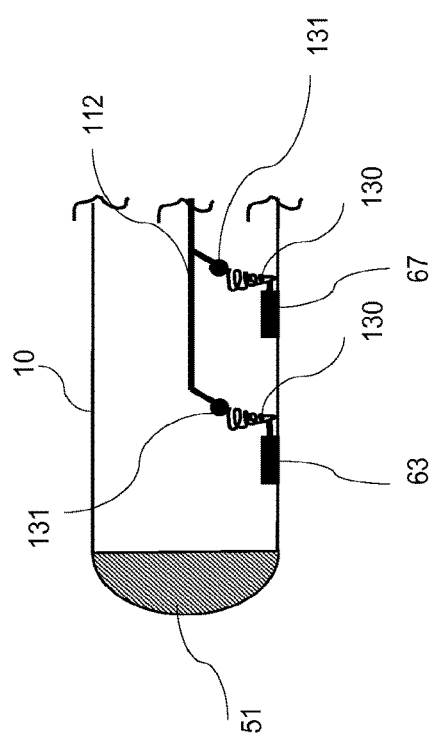
FIG. 13(A) schematically illustrates a cross section of an exemplary embodiment of the epicardial pacing catheter comprising a deployable screw or the like in an un-deployed state.

FIG. 13(A) schematically illustrates a cross section of an exemplary embodiment of the epicardial pacing catheter 10 of the epicardial pacing system comprising a deployable stabilization means in an un-deployed state. The deployable stabilization means comprises a number of screws 130 in communication with an anode 63 and cathode 67. The screws 130, anode 63, and cathode 67 comprise conductive materials, such as, but not limited to, copper, platinum, gold, silver and/or iridium, and/or alloys thereof.

The stabilization means further comprises a stabilizer actuator, wherein said stabilizer actuator deploys the screws 130 in communication with the anode 63 and cathode 67. Though the stabilizer actuator is illustrated as an electrode pull-wire 112 in communication with a gear 131, the stabilizer actuator may comprise any longitudinal member in communication with at least one of the following: gear, hinge, joint, rack and pinion, pulley, linear actuator, or linear-rotational actuator, or any combination thereof. Further, the longitudinal member may be, for example, a push-rod, pull-wire, wire, string, rope, pole, thread, filament, cord, strand, or other means known in the art. The stabilizer actuator may further comprise a micro electrical mechanical system (MEMS).

It should be appreciated that the screw devices may comprise a number of elements such as, but not limited thereto, any translatable protrusion or extension for instance. Some non-limiting examples may include: toggle, press, slide, spring, stud, post, tongue, projection, pedestal, protuberance, contact, or the like.

In an embodiment, an electrode pull-wire 112 extends longitudinally from the most proximal portion of the epicardial pacing lead 10 to the most distal electrode 43, which may be an anode 63 or cathode 67. The electrode pull-wire 112 may be a longitudinal structure, such as, but not limited to, a push-rod, pull-rod, wire, string, or rope. The electrode pull-wire 112 may be made of a conductive material having high tensile strength as is known in the art. The electrode-pull wire 112 may further be controllably connected to a control means (as shown, for example, in FIG. 15) in communication with the epicardial pacing catheter 10 and epicardial pacing system. The control means may be used to control the deployment of the screws 130 in communication with the anode 63 and cathode 67.

The epicardial pacing catheter 10 further comprises an insulating distal tip 51 in communication with the epicardial pacing catheter.

When the screws 130 are in the non-deployed state, the epicardial pacing catheter 10 may be moved or navigated within the middle mediastinum. In this way, the epicardial pacing catheter 10 can be inserted, placed, navigated, translated, rotated or removed from the pericardial sack.

Figure 13B:
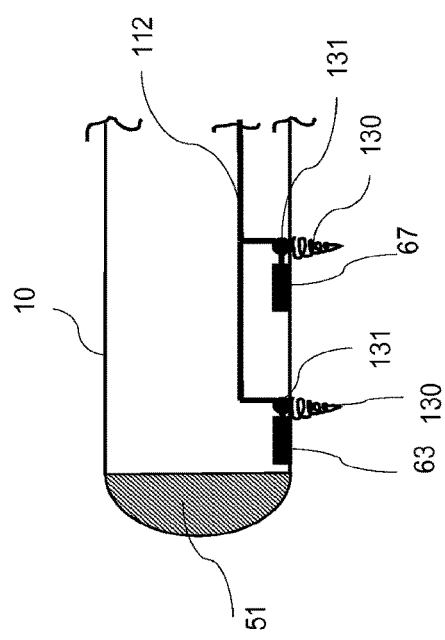
FIG. 13(B) schematically illustrates a cross section of an exemplary embodiment of the epicardial pacing catheter comprising a deployable screw or the like in a fully-deployed state.

FIG. 13(B) schematically illustrates a cross section of an exemplary embodiment of the epicardial pacing catheter 10 comprising fully-deployed screws 130 in communication with the anode 63 and cathode 67. When the electrode pull-wire 112 is pushed toward the distal end of the epicardial pacing catheter 10, the gears 131 are activated and the screws 130 are rotationally-actuated. This causes the screws 130 to engage proximate anatomical structures, such as the epicardial wall. When the screws 130 are in the fully-deployed state, the rotational orientation of the distal portion of the epicardial pacing catheter 10 remains fixed in place relative to the surface of the heart. The electrical energy is transmitted from the anode 63 and cathode 67 through the screws 130 and into the heart.

It should be appreciated that in FIGS. 13(A) and (B) any number of deployable screws 130 may be present as desired or required to pace any number of locations on the heart of a patient.

FIG. 14(A) schematically illustrates a cross section of an exemplary embodiment of the epicardial pacing catheter 10 epicardial pacing system comprising a deployable stabilization means in an un-deployed state. The deployable stabilization means comprises an anode 63 and cathode 67 in communication with a hook 124. The hooks 124, anode 63, and cathode 67 comprise conductive materials, such as, but not limited to, copper, platinum, gold, silver and/or iridium, or alloys thereof.

The deployable stabilization means further comprises a stabilizer actuator, wherein said stabilizer actuator deploys the anode 63 and cathode 67 in communication with the hooks 124. Though the stabilizer actuator is illustrated as an electrode pull-wire 112 and second electrode pull-wire 113 in communication with a number of joints 121, and hinges 122, the stabilizer actuator may comprise any longitudinal member in communication with at least one of the following: gear, hinge, joint, rack and pinion, pulley, linear actuator, or linear-rotational actuator, or any combination thereof. Further, the longitudinal member may be, for example, a push-rod, pull-wire, wire, string, thread, filament, cord, strand, rope, pole, or other means known in the art. The stabilizer actuator may further comprise a micro electrical mechanical system (MEMS).

In an embodiment, an electrode pull-wire 112 and second electrode pull-wire 113 extend longitudinally from the most proximal portion of the epicardial pacing lead 10 to the most distal anode 63 and cathode 67 respectively. The electrode pull-wire and second electrode pull-wire 113 are in communication with a number of joints 121, the joints 121 in further communication with a number of hinges 122. The electrode pull-wire 112 and second electrode pull-wire 113 may comprise longitudinal structures, such as, but not limited to, push-rods, pull-rods, wires, thread, filament, cord, strand, strings, or ropes. The electrode pull-wire 112 and second electrode pull-wire 113 may be made of a conductive material having high tensile strength as is known in the art. The electrode-pull wire 112 and second electrode pull-wire 113 may further be controllably connected to a control means (for example, as shown in FIG. 15) in communication with the epicardial pacing catheter 10 and epicardial pacing system. The control means may used to control the deployment of the anode 63 and cathode 67 in communication with hooks 124.

The epicardial pacing catheter 10 further comprises an insulating distal tip 51 in communication with the epicardial pacing catheter. The epicardial pacing catheter 10 may further comprise a number of bumpers 120 in communication with the epicardial pacing catheter 10. The bumpers 120 enable the epicardial pacing catheter 10 to sit on the surface of the heart in a non-deployed state without allowing the anode 63 or cathode 67 to communicate with the heart.

When the deployable anode 63 and cathode 67 are in the non-deployed state, the epicardial pacing catheter 10 may be moved or navigated within the middle mediastinum. In this way, the epicardial pacing catheter 10 can be inserted, placed, navigated, translated, rotated or removed from the pericardial sack.

FIG. 14(B) schematically illustrates a cross section of an exemplary embodiment of the epicardial pacing catheter 10 comprising a deployable anode 63 and cathode 67 in a fully-deployed state. When the electrode pull-wire 112 and second electrode pull-wire 113 are pulled toward the proximal end of the epicardial pacing catheter 10, the anode 63 and cathode 67 are splayed outward to a 90 degree angle. This causes the anode 63 and cathode 67 to separate from the catheter body, allowing the hooks 124 to engage proximate anatomical structures, such as the epicardial wall. When the deployable anode 63 and cathode 67 are in the fully-deployed state, the rotational orientation of the distal portion of the epicardial pacing catheter 10 remains fixed in place relative to the surface of the heart. The electrical energy is transmitted from the anode 63 and cathode 67 through the hooks 124 and into the heart.

It should be appreciated that in FIGS. 14(A) and (B) any number of deployable anodes 63 and cathodes 67 may be present as desired or required to pace any number of locations on the heart of a patient.

It should be appreciated that when the electrode pull-wire 112 and second electrode pull-wire are pushed toward the distal end of the epicardial pacing catheter 10, the anode 63 and cathode 67 are drawn back into place within the catheter 10.

It should be appreciated that regarding deployment discussed throughout, varying degrees of deployment may be achieved or implemented as desired or required.

FIG. 15(A) schematically illustrates an example embodiment of an external control handle 150 (that may be associated with, although not shown, the epicardial pacing catheter of the system). The epicardial pacing catheter and system further comprises a control means, wherein said control means is an external control handle 150. The external control handle 150 may be in communication with the most proximal point 73 of the epicardial pacing catheter 10. The external control handle 150 may have integral to it the distal steering control means 154, the proximal control means 154, the irrigation control means (not shown) and the control means for the stabilization means 151. The stabilization control means 154 may be used to regulate the degree of extension of said stabilization means via a pull-wire or pushrod arrangement or some other suitable tensioning or actuating means know in the art. The external control handle 150 may further comprise a pull-rod control aperture 152, wherein a tab deployment rod 64 and second tab deployment rod (not shown) may be inserted.

The external control handle 150 is preferably sized to be grasped, held and operated by a user. It should be appreciated that other control and operating interface members, devices, or means may be utilized for the handle. Attached to the proximal end of the control handle 150 is the handle proximal port (not shown) from which anode wires 62 and cathode wires 67 extend in order to make electrical connections to diagnostic or electrical devices (not shown). Electrical wires (for example, shown in FIGS. 6, 7, and 11) may extend through the proximal portion to each of the electrodes 43 of the epicardial pacing catheter 10.

FIG. 15(B) schematically illustrates an example embodiment of the proximal steering control means 153 integral to the control handle 150. The proximal steering control means 153 is controllably connected to the first proximal steering pull-wire 70 and second proximal steering pull-wire 71.

FIG. 15(C) schematically illustrates an example embodiment wherein the proximal steering control means 153 integral to the control handle 150 has been activated. As the proximal steering control means 153 is activated by a user, the first proximal steering pull-wire 70 becomes taught, and the second proximal steering pull-wire 71 loosens, creating slack 155. Both the first proximal steering pull-wire 70 and second proximal steering pull-wire 71 extend longitudinally through the control handle 150, into the epicardial pacing catheter 10, and are anchored at the proximal point of curvature 42. As the first steering pull-wire 70 becomes taught, the epicardial pacing catheter bends toward the proximal steering anchor and around the proximal point of curvature 42.

For example, the control handle may have channels for the steering pull wires and thumb wheel knobs for tightening or loosening the pull wires.

One skilled in the art can see that many other embodiments of means and methods for using the epicardial pacing catheter 10 of the epicardial pacing system according to the technique of the technology, and other details of construction and use thereof, constitute non-inventive variations of the novel and insightful conceptual means, system and technique which underlie the present invention.

The devices, systems, compositions, computer program products, and methods of various embodiments of the invention disclosed herein may utilize aspects disclosed in the following references, applications, publications and patents and which are hereby incorporated by reference herein in their entirety:
1. U.S. Pat. No. 6,973,352 B1 to Tsutsui, D., et. al., entitled "Steerable Cardiac Pacing and Sensing Catheter and Guidewire for Implanting Leads", Dec. 6, 2005.
2. U.S. Pat. No. 7,264,587 B2 to Chin, A., entitled "Endoscopic Subxiphoid Surgical Procedures", Sep. 4, 2007.
3. U.S. Pat. No. 7,226,458 to Kaplan, et al., issued May 2007.
4. U.S. Pat. No. 7,226,448 to Bertolero, et. al., issued May 2007.
5. U.S. Pat. No. 7,142,919 to Hine, et al., issued May 2006.
6. U.S. Pat. No. 7,130,699 to Huff, et al., issued October 2006.
7. U.S. Pat. No. 7,120,504 to Osypka, issued October 2006.
8. U.S. Pat. No. 7,101,362 to Vinne, issued September 2006.
9. U.S. Pat. No. 7,090,637 to Danitz, et al., issued August 2006.
10. U.S. Pat. No. 7,089,063 to Lesh, et al., issued August 2006.
11. U.S. Pat. No. 7,059,878 to Hendrixson, issued August 2006.
12. U.S. Pat. No. 7,041,099 to Thomas, et al., issued May 2006.
13. U.S. Pat. No. 7,027,876 to Casavant, et al., issued April 2006.
14. U.S. Pat. No. 7,008,418 to Hall, et al., issued March 2006.
15. U.S. Pat. No. 6,973,352 to Tsutsui, et al., issued December 2005.
16. U.S. Pat. No. 6,936,040 to Kramm, et al., issued August 2005.
17. U.S. Pat. No. 6,921,295 to Sommer, et al., issued July 2005.
18. U.S. Pat. No. 6,918,908 to Bonner, et al., issued August 2005.
19. U.S. Pat. No. 6,899,710 to Hooven, issued May 2005.
20. U.S. Pat. No. 6,876,885 to Swoyer, et al., issued May 2005.
21. U.S. Pat. No. 6,868,291 to Bonner, et al., issued March 2005.
22. U.S. Pat. No. 6,837,886 to Collins, et al., issued January 2005.
23. U.S. Pat. No. 6,835,193 to Epstein, et al., issued December 2004.
24. U.S. Pat. No. 6,527,767 to Wang, et al., issued March 2003.
25. U.S. Pat. No. 6,314,963 to Vaska, et al., issued November 2001.
26. U.S. Pat. No. 6,270,476 to Santoianni, et al., issued August 2001.
27. U.S. Pat. No. 6,263,241 to Rosborough, et al., issued July 2001.
28. U.S. Pat. No. 6,237,605 to Vaska, et al., issued May 2001.
29. U.S. Pat. No. 6,123,084 to Jandak, et al., issued September 2000.
30. U.S. Pat. No. 6,036,685 to Mueller, et al., issued March 2000.
31. U.S. Pat. No. 5,733,280 to Avitall, issued March 1998.
32. U.S. Pat. No. 5,213,570 to Van Deripe, et al., issued May 1993.
33. U.S. Patent Application Publication No. 2007/0038052 to Swoyer, et al., issued February 2007.
34. U.S. Patent Application Publication No. 2006/0270900 to Chin, et al., issued November 2006.
35. U.S. Patent Application Publication No. 2006/0122591 to Keidar, issued June 2006.
36. U.S. Patent Application Publication No. 2006/0025762 to Mohan, et al., February 2006.
37. U.S. Patent Application Publication No. 20040267326 to Ocel, et al., issued December 2004.
38. U.S. Patent Application Publication No. 2004/0138526 to Guenst, issued July 2004.
39. U.S. Patent Application Publication No. 2004/0087831 to Michels, et al., issued May 2004.
40. U.S. Patent Application Publication No. 2003/0069572 to Wellman, et al., issued April 2003.
41. U.S. Patent Application Publication No. 2003/0065318 to Pendekanti, issued April 2003.
42. U.S. Patent Application Publication No. 2003/0028187 to Vaska, et al., issued February 2003.
43. International Patent Application Publication No. WO97/33526, issued September 1997.
44. International Patent Application Publication No. WO95/15115, issued June 1995.
45. International Patent Application Publication No. WO93/20878, issued October 1993.
46. International Patent Application Publication No. WO87/04081, issued July 1987. 47. M. Tomaske et al., "Do Daily Threshold Trend Fluctuations of Epicardial Leads Correlate with Pacing and Sensing Characteristics in Paediatric Patients," Europace, doi: 10.1093/europace/eum100, (2007).
48. A. d'Avila et al., "Transthoracic Epicardial Catheter Ablation of Ventricular Tachycardia," Heart Rhythmn, Vol. 3, pp. 1110-1111, (2006).
49 E. Sosa et al., "Epicardial Mapping and Ablation Techniques to Control Ventricular Tachycardia," Journal of Cardiovascular Electrophysiology, Vol. 16, pp. 449-452, (2005).
50. S. Mahapatra et al., "Incidence and Predictors of Cardiac Perforation after permanent Pacemaker Placement," Heart Rhythm, Vol. 2, pp. 907-911, (2005).
51. D. L. Packer et al., "Multimodality 3-D Ultrasound and Computed Tomographic Image Fusion: A Novel Basis for Catheter Navigation and Electroanatomic Mapping," Circulation, Vol. 112, p. U684, (2005).
52. E. Sosa et al., "Nonsurgical Transthoracic Epicardial Approach in Patients with Ventricular Tachycardia and Previous Cardiac Surgery," Journal of Interventional Cardiac Electrophysiology, Vol. 10, pp. 281-288, (2004).
53. J. Derose, Jr. et al., "Robotically Assisted Left Ventricular Epicardial Lead Implantation for Biventricular Pacing: the Posterior Approach," Annals of Thoracic Surgery, Vol. 77, pp. 1472-1474, (2004).
54. B. Hansky et al., "Lead Selection and Implantation Technique for Biventricular Pacing," European Heart Journal Supplements, Vol. 6, D112-D116, (2004).
55. H. Mair et al., "Epicardial Lead Implantation Techniques for Biventricular Pacing via Left Lateral Mini-Thoracotomy, Video-Assisted Thoracoscopy, and Robotic Approach, The Heart Surgery Forum, Vol. 6, #2003-4883, (2003).
56. A. V. Sarabanda, et al., "Efficacy and Safety of Circumferential Pulmonary Vein Isolation Using a Novel Cryothermal Balloon Ablation System" Journal of the American College of Cardiology, Vol. 46, pp. 1902-1912 (2005).

57. S. Mahapatra et al., G. T. Gillies, "Access Device and Manometric Monitoring System for Epicardial Electrophysiology: Improved Porotype and Use in Human Trials", Technical Report UVA/640419/MAE08/102.

It should be appreciated that various sizes, dimensions, contours, rigidity, shapes, flexibility and materials of any of the embodiments discussed throughout may be varied and utilized as desired or required.

It should be appreciated that the catheter device and epicardial system and their related components discussed herein may can take on all shapes along the entire continual geometric spectrum of manipulation of x, y and z planes to provide and meet the anatomical and structural demands and requirements.

EXAMPLES AND EXPERIMENTAL RESULTS

Practice of the invention will be still more fully understood from the following examples and experimental results, which are presented herein for illustration only and should not be construed as limiting the invention in any way.

Example No. 1

Step 1—Access and place a guidewire in the pericardial space using our EpiNeedle Access system.

Step 2—Use a sheath, preferably our EpiSheath, or a general long 8 Fr sheath to place over the guidewire and maintain access.

Step 3—Place the lead of the subject invention with handle though the sheath.

Step 4—Guide the lead in the epicardial space using the two steering points and the sheath under fluoroscopic guidance (although this lead may be guided via one or more other imaging methods to include ICE, CT, MRI, Visual Endoscopy, or Echo Methods). The lead should be advanced along the border of the heart apically to base along the LV. Once it crosses the AV groove to the LA it should be deflected downward and advanced through the transverse sinus. Once across the transverse sinus it will need to be deflected up to the SVC and then down to the RA and finally the RV.

Step 5—Slide the sheath back to the inferior portion of the RV.

Step 6—At this point the handle should be hooked up to an EP analyzer. The lead should be clocked for a more anterior position or counter-clocked for a more posterior position until the largest LV signals are found. If multi-chamber pacing is sought one should pick a point when at least two poles of the LV, and of each other chamber, has an amplitude of at least 1 mV in the atrium and 5 mV in the ventricle. Note there is no need for all points to have high amplitudes. Next, the tabs should be deployed. This should push the lead more tightly against the heart and actually increase the voltage. Then, pacing should be attempted in the LV. If threshold is less than 2.5 V it is a good site on any pole. The same should then be done with the other points. If no point is good the tab should be let down and then the lead repositioned.

Step 7—Once a good position is found the handle should be removed and the sheath withdrawn completely outside of the patient.

Step 8—The lead should be plugged into either a custom ICD/BiV or attached to our wire interface for a standard ICD. The poles that are not used to pace should be plugged in this case. In the custom ICD, all poles would be active and the user (or an automated system) may decide when to pace.

Step 9—The lead extender to the ICD would then either be tunneled back to the ICD in the shoulder (or elsewhere), placed by the nearby abdominal ICD. Or a battery-powered wireless box will be used to communicate with the main ICD in the shoulder. At this point the patient should be recovered. No stitch is needed for the lead access.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary.

Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. An epicardial pacing system, said system comprising:
an epicardial pacing catheter configured to be disposed in the body of a subject and configured for use in electrical pacing of the heart in at least three locations on the epicardial surface, said epicardial pacing catheter including:

a proximal portion, a distal portion, and a longitudinal structure there between, wherein the proximal portion, the distal portion, and the longitudinal structure have requisite flexibility for deployment within the subject;

a plurality of electrodes in communication with said distal portion;

a stabilizer including deployable members configured to transition between a retracted position and a deployed position via a hinge device while disposed in the body of the subject, wherein the deployable members comprise at least one outward facing bumper tab and at least one inward facing friction tab and wherein the at least one inward facing friction tab exposes a lubricious surface when in the retracted position and further exposes a textured surface when transitioned to the deployed position, wherein the textured surface of the at least one inward facing friction tab comprises a rough surface having a larger coefficient of friction than the lubricous surface; and stabilizer actuators configured to allow an operator of said epicardial pacing system to deploy said deployable members, wherein the stabilizer actuators each include a longitudinal member that is in communication with the hinge device and is configured to deploy a corresponding deployable member of the deployable members to the deployed position via the hinge device.

2. The system of claim 1, wherein said deployable members (a) in said deployed position impede movement of said distal portion while disposed in the body of the subject via contact with or adherence to anatomical structures, and (b) in said retracted position ease movement of said distal portion while disposed in the body of the subject compared to said deployed position.

3. The system of claim 1, wherein said stabilizers are operable to transition said deployable members between said retracted position and said deployed position by at least one of rotating said deployable members away from a surface of said distal portion, or by deploying at least part of said deployable members from within said distal portion.

4. The system of claim 1, wherein when each of the plurality of electrodes is coupled to a point on the heart, the epicardial pacing catheter is configured to deliver a signal to the left ventricle wherein the signal has an amplitude of at least 1 mV in the atrium and wherein the signal has an amplitude of at least 5 mV in the ventricle.

5. The system of claim 1, wherein the electrical pacing catheter is configured for use in at least three locations on the epicardial surface simultaneously.

* * * * *